(12) United States Patent
Kang et al.

(10) Patent No.: US 11,627,903 B2
(45) Date of Patent: Apr. 18, 2023

(54) METHOD FOR DIAGNOSING COGNITIVE DISORDER, AND COMPUTER PROGRAM

(71) Applicants: IMEDISYNC, INC., Seoul (KR); CHUNG ANG UNIVERSITY INDUSTRY ACADEMIC COOPERATION FOUNDATION, Seoul (KR)

(72) Inventors: Seung Wan Kang, Seoul (KR); Young Chul Youn, Seoul (KR)

(73) Assignees: IMEDISYNC, INC., Seoul (KR); CHUNG ANG UNIVERSITY INDUSTRY ACADEMIC COOPERATION FOUNDATION, Seoul (KR)

(*) Notice: Subject to any disclaimer, the term of this patent is extended or adjusted under 35 U.S.C. 154(b) by 434 days.

(21) Appl. No.: 16/868,804

(22) Filed: May 7, 2020

(65) Prior Publication Data
US 2020/0260977 A1    Aug. 20, 2020

Related U.S. Application Data

(63) Continuation of application No. PCT/KR2018/016788, filed on Dec. 27, 2018.

(30) Foreign Application Priority Data

Sep. 14, 2018  (KR) .................... 1020180110468

(51) Int. Cl.
*A61B 5/316*    (2021.01)
*A61B 5/00*    (2006.01)
(Continued)

(52) U.S. Cl.
CPC .............. *A61B 5/316* (2021.01); *A61B 5/369* (2021.01); *A61B 5/4088* (2013.01); *A61B 5/7267* (2013.01); *A61B 5/374* (2021.01)

(58) Field of Classification Search
CPC ....... A61B 5/316; A61B 5/369; A61B 5/4088; A61B 5/7267; A61B 5/374; A61B 5/4848; A61B 5/7257; A61B 5/7275; G16H 50/50
See application file for complete search history.

(56) References Cited

U.S. PATENT DOCUMENTS

2009/0156954 A1   6/2009 Cox et al.
2014/0107494 A1*  4/2014 Kato ................... A61B 5/4088
                                        600/300
(Continued)

FOREIGN PATENT DOCUMENTS

JP      2016106940       6/2016
KR   10-2010-0026426    3/2010
(Continued)

OTHER PUBLICATIONS

International Search Report for International Application PCT/KR2018/016788, dated Jun. 14, 2019.
(Continued)

*Primary Examiner* — Md K Talukder
(74) *Attorney, Agent, or Firm* — Guntin & Gust, PLC; Miyoung Shin

(57) ABSTRACT

Provided is a cognitive impairment diagnosis method including: receiving an electroencephalogram signal of a user by a cognitive impairment diagnosis device; preprocessing the electroencephalogram signal by the cognitive impairment diagnosis device; extracting features, by the cognitive impairment diagnosis device, from the electroencephalogram signal by using a brain connectivity-based analysis method; and outputting cognitive impairment diagnosis information of the user by the cognitive impairment diagnosis device, on the basis of features having a causal (Continued)

relationship with the cognitive impairment diagnosis information, among the extracted features.

2 Claims, 16 Drawing Sheets

(51) Int. Cl.
  *A61B 5/369* (2021.01)
  *A61B 5/374* (2021.01)

(56) References Cited

U.S. PATENT DOCUMENTS

| | | | |
|---|---|---|---|
| 2015/0088024 A1* | 3/2015 | Sackellares | G06K 9/00523 600/544 |
| 2017/0258390 A1* | 9/2017 | Howard | A61B 5/369 |
| 2017/0340262 A1 | 11/2017 | Momose et al. | |
| 2019/0209097 A1* | 7/2019 | Martien | A61B 5/7282 |
| 2020/0237247 A1* | 7/2020 | Glik | A61B 5/4088 |
| 2020/0260977 A1* | 8/2020 | Kang | A61B 5/7275 |

FOREIGN PATENT DOCUMENTS

| | | |
|---|---|---|
| KR | 101721230 | 3/2017 |
| KR | 1020170050150 | 5/2017 |
| KR | 10-1796055 | 11/2017 |
| KR | 1020180002102 | 1/2018 |

OTHER PUBLICATIONS

Office Action Issued in Corresponding KR Application No. 10-2018-0170963, dated Sep. 3, 2020.

\* cited by examiner

METHOD FOR DIAGNOSING COGNITIVE DISORDER, AND COMPUTER PROGRAM

CROSS-REFERENCE TO RELATED APPLICATIONS

This application is a continuation of PCT Application No. PCT/KR2018/016788, filed Dec. 27, 2018, which claims priority to Korean Patent Application No. 10-2018-0110468, filed Sep. 14, 2018, the disclosures of which are hereby incorporated by reference in their entireties.

TECHNICAL FIELD

The present disclosure relates to a cognitive impairment diagnosis method and a computer program.

BACKGROUND

The number of patients with degenerative brain diseases including dementia patients has rapidly increased with the increase in an aging population, and social cost has also increased accordingly. The social cost of dementia has been reported to exceed the sum of costs of three types of diseases such as cancer, heart disease, and cerebral stroke.

Currently, medical technologies are used to diagnose whether degenerative brain diseases occur or whether cognitive impairments occur, using brain images, answers to questions, or the like. Diagnoses using this method diagnose only whether users' cognitive impairments occur but may not diagnose the exact disease names, such as degenerative brain diseases, Parkinson's diseases, Alzheimer's diseases, and the like, or may not make early diagnoses at the initial stages of the diseases.

SUMMARY

Provided are a cognitive impairment diagnosis method and a cognitive impairment diagnosis modeling method that diagnose patients and monitor progressions of disease stages and responses to treatments.

A cognitive impairment diagnosis method according to aspects of the present disclosure may receive an electroencephalogram signal of a user, analyze the electroencephalogram signal, determine a degree of a cognitive impairment and a cause of the cognitive impairment for the analyzed electroencephalogram signal using a cognitive impairment prediction function, synthesize analyzed results to generate diagnosis information about the cognitive impairment and a dementia symptom of the user, and generate the generated diagnosis information related to the cognitive impairment as a single report.

According to embodiments of the present invention, a cognitive impairment diagnosis modeling method may receive input data including a cognitive impairment diagnosis modeling electroencephalogram signal and cognitive impairment-related result values, analyze the input data to extract features, generate and learn causal relationships between the features and the cognitive impairment-related result values, and update a cognitive impairment diagnosis model using the cognitive impairment diagnosis modeling electroencephalogram signal and the cognitive impairment-related result values.

A computer program according to an aspect of the present disclosure may be stored in a medium to execute any one of methods according to aspects of the present disclosure using a computer.

Other methods, other systems, and computer-readable recording media recording thereon the computer program for executing the method may be further provided.

Other aspects, features, and advantages than those described above will become apparent from the following drawings, claims, and detailed description of the present disclosure.

According to an aspect of the present disclosure, a cognitive impairment diagnosis method may include: receiving an electroencephalogram signal of a user by a cognitive impairment diagnosis device; preprocessing the electroencephalogram signal by the cognitive impairment diagnosis device; extracting features, by the cognitive impairment diagnosis device, from the preprocessed electroencephalogram signal by using a brain connectivity-based analysis method; and outputting cognitive impairment diagnosis information of the user by the cognitive impairment diagnosis device, on the basis of features having a causal relationship with the cognitive impairment diagnosis information, among the extracted features.

The outputting of the cognitive impairment diagnosis information may include
outputting the cognitive impairment diagnosis information of the user by the cognitive impairment diagnosis device, on the basis of a feature related to whether a mild cognitive impairment occurs and a feature related to a probability of a cognitive impairment that may develop into a significant cognitive impairment, wherein the features are selected through a cognitive impairment diagnosis model that is previously trained.

The cognitive impairment diagnosis model may be connected to hidden data on the basis of a causal relationship inferred by machine learning when inferring one or more factors included in the electroencephalogram signal as pieces of output data related to a cognitive impairment.

The hidden data may not be included in the electroencephalogram signal that is input data and/or the cognitive impairment diagnosis information that is output data and may include features, characteristics, factors, or data used in an inference process from the electroencephalogram signal to the cognitive impairment diagnosis information.

A cognitive impairment diagnosis method and a cognitive impairment diagnosis modeling method according to embodiments of the present disclosure may identify users of an MCI stage or a high dementia risk group at a community level.

Also, the cognitive impairment diagnosis method and the cognitive impairment diagnosis modeling method according to the embodiments of the present disclosure may classify major pathophysiological types of users with impaired cognitive functions.

In addition, the cognitive impairment diagnosis method and the cognitive impairment diagnosis modeling method according to the embodiments of the present disclosure may evaluate severities of multi-domain cognitive impairments, ischemic changes, and cortical atrophy.

Moreover, according to embodiments of the present disclosure, a probability of progression from MCI to dementia may be predicted.

Furthermore, the cognitive impairment diagnosis method and the cognitive impairment diagnosis modeling method according to the embodiments of the present disclosure may select subjects of types who respond better to a test drugs in clinical tests for dementia treatment drugs.

Also, the cognitive impairment diagnosis method and the cognitive impairment diagnosis modeling method according to the embodiments of the present disclosure may monitor drug responses to neurodegeneration, ischemia, cognitive functions, or neurological recovery.

DETAILED DESCRIPTION OF EMBODIMENTS

Figure 1:
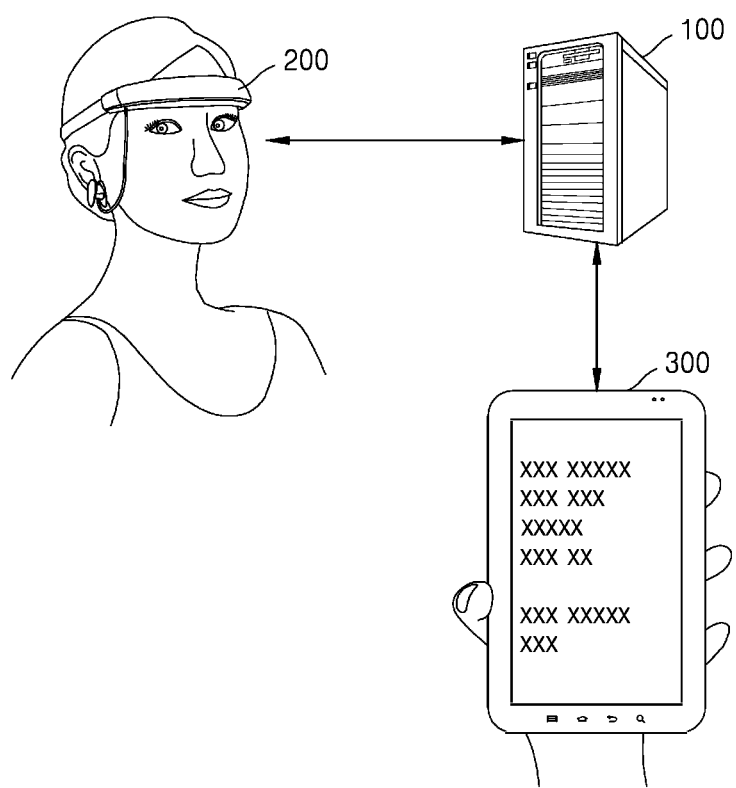
FIG. 1 illustrates a network environment of a cognitive impairment diagnosis system according to embodiments.

While example embodiments are capable of various modifications and alternative forms, embodiments thereof are shown by way of example in the drawings and will herein be described in detail. The effects and features of the present disclosure and the accompanying methods thereof will become apparent from the following description of the embodiments, taken in conjunction with the accompanying drawings. However, the present disclosure is not limited to the embodiments described below, and may be embodied in various modes.

Although the terms first, second, etc. may be used to describe various elements or components, these elements or components should not be limited by these terms. These terms are only used to distinguish one element or component from another element or component. For example, a first element or component could be termed a second element or component, and, similarly, a second element or component could be termed a first element or component without departing from the scope of example embodiments. As used herein, the term "and/or" includes any and all combinations of one or more of the associated listed items.

The terminology used herein is for the purpose of describing particular embodiments only and is not intended to be limiting and/or restricting of example embodiments. The singular forms are intended to include the plural forms as well, unless the context clearly indicates otherwise. It will be understood that the terms "comprises," "includes," "have," etc. when used in this specification, specify the presence of stated features, integers, steps, operations, elements, and/or components, but do not preclude the presence or addition of one or more other features, integers, steps, operations, elements, components, and/or groups thereof.

When a part is referred to as being connected to another part, it may be directly connected to the other part or intervening elements may be present. Also, when a part is referred to as including a certain component, this means that other components may be further included rather than excluding other components unless the context clearly indicates otherwise. As used herein, the terms " . . . part," "module," etc. refers to a unit that processes at least one function or operation, which may be embodied as hardware, software, or a combination of hardware and software.

An electroencephalogram is a kind of biological wave output by living things, and human electroencephalograms also appear as a kind of voltage change in the scalp area of a human body. Normally, an electroencephalogram appears in amplitude of a voltage range of about 10 μV to about 200 μV in a frequency range of about 0 Hz to about 60 Hz. An electroencephalogram of the human body is classified into gamma ($\gamma$) wave, alpha ($\alpha$) wave, beta ($\beta$) wave, delta ($\delta$) wave, theta ($\theta$) wave, and the like according to the frequency range thereof. The delta wave is an electroencephalogram of less than about 4 Hz and mainly occurs during sleep, the theta wave is an electroencephalogram in a range of about 4 Hz to about 8 Hz and mainly occurs in a blank state, the alpha wave is an electroencephalogram with a frequency of about 8 Hz to about 13 Hz and mainly occurs in a stable state, the beta wave is an electroencephalogram with a frequency of 13 Hz or more and mainly occurs in an active state, and a high beta wave is an electroencephalogram with a frequency of 25 Hz and mainly occurs when excited or stressed.

As used herein, an electroencephalogram signal may include information about a plurality of positions constituting a brain, channels respectively allocated to the plurality of positions constituting the brain, and bands of frequencies constituting an electroencephalogram.

The electroencephalogram signal may further include one or more of absolute power and relative power of a power spectrum of the electroencephalogram, the magnitude of each frequency component of the power spectrum of the electroencephalogram, an alpha peak frequency of the electroencephalogram, ratios and coupling between different frequency bands of the electroencephalogram, connectivity of each position of a ring electroencephalogram, and complexity of the electroencephalogram. Also, for electrical signals in the brain calculated using various techniques reconstructing an electric signal source in the brain on the basis of an electroencephalogram measured from the scalp, the electroencephalogram signal may include one or more of a current concentration in each frequency band thereof, ratios and coupling between absolute or relative power and frequency bands, connectivity and synchronicity of each area, complexity, and the like.

As described herein, the connectivity of the brain may be acquired through a process of constituting a brain network and interpreting the same topologically. The connectivity of the brain may include structural connectivity and functional connectivity of the brain on the basis of a brain image. The functional connectivity of the brain may be acquired using a point that electrophysiological activity appears over time with particular rules between different areas. The functional connectivity of the brain may be acquired by calculating a pattern in which different brain areas are functionally connected and activated together, by statistical, topological, entropy-based effective connectivity analyses, and the like to calculate the same as a close measure between brain areas.

As used herein, models and functions refer to statistics-based formula functions for estimating objective variables or outputs by machine learning.

FIG. 1 illustrates a network environment of a cognitive impairment diagnosis system according to embodiments.

The cognitive impairment diagnosis system may include a cognitive impairment diagnosis device 100, an electroencephalogram measurement device 200, and a user terminal 300 to diagnose degrees and causes of cognitive impairments of users.

The cognitive impairment diagnosis device 100 diagnoses the degrees of the cognitive impairments of the users considering biological ages of the users. The cognitive impairment diagnosis device 100 may determine the degrees of the cognitive impairments and the causes of the cognitive impairments by using electroencephalogram signals received from the electroencephalogram measurement device 200 as inputs. The cognitive impairment diagnosis device 100 may determine the degrees and the causes of the cognitive impairments of the users using a cognitive impairment diagnosis model generated by machine learning. Here, the degrees of the cognitive impairments are measures indicating the degrees of the cognitive impairments of the users, may be represented by evaluating the cognitive impairments from initial stages to severe stages, and may include possibilities of future occurrences. The degrees of the cognitive impairments may be determined using causal relationships between biological information about ages, genders, and the like of the users and social information about residential environments, occupations, educational backgrounds, and the like of the users. The cognitive impairment diagnosis device 100 may selectively provide cognitive impairment-related information selected by a connected user. The cognitive impairment-related information may be provided for a user who requests the cognitive impairment-related information, and a drug and a treatment method matching an input degree and cause of a cognitive impairment may be provided. Cognitive impairment-related information of the user may be searched for from input user information, a drug and a treatment method corresponding to the cognitive impairment-related information may be provided for the user, and if the user has a mild cognitive impairment, cognitive impairment-related prediction information may also be provided for the user.

The electroencephalogram measurement device 200 may measure an electroencephalogram signal of a user. The electroencephalogram measurement device 200 refers to a device that is attached to a frontal lobe, a parietal lobe, a temporal lobe, and an occipital lobe to measure electroencephalograms noninvasively and may freely change a position of a electroencephalogram measurement terminal for electroencephalogram measurements according to the head of the user to measure electroencephalograms. Terminals of the electroencephalogram measurement device 200 may be provided by being connected by an additional cable or may be wirelessly connected and may be arranged at preset intervals in a band unit. The electroencephalogram signal measured by the electroencephalogram measurement device 200 may include information about connectivity between areas of a brain and/or information about classification into a delta wave, a theta wave, an alpha wave, a beta wave, and a gamma wave.

The user terminal 300 is an electronic device that accesses the cognitive impairment diagnosis device 100 to transmit a signal for an input/output device of a vehicle of the user in wired and wireless communication environments and may be at least one selected from a smartphone, a tablet personal computer (PC), a mobile phone, a video phone, an e-book reader, a desktop PC, a laptop PC, a netbook computer, a workstation, a server, a personal digital assistant (PDA), a portable multimedia player (PMP), an MP3 player, a mobile medical device, a camera, and a wearable device. The user terminal 300 includes a processor, a storage medium, a communication module, and an input/output device and communicates with the cognitive impairment diagnosis device 100.

The user terminal 300 receives output data from the cognitive impairment diagnosis device 100 and outputs the output data. The user terminal 300 may access the cognitive impairment diagnosis device 100 using a pre-installed program or may execute a program distributed by the cognitive impairment diagnosis device 100. The user terminal 300 may receive an account (an ID, biological information, a token, or the like) for cognitive impairment diagnosis services in advance, may access the cognitive impairment diagnosis device 100 using the account, and may be provided with the cognitive impairment-related information of the user. Through the cognitive impairment diagnosis device 100, the user may be provided with the cognitive impairment-related information including whether a cognitive impairment occurs, a degree of the cognitive impairment, a cause of the cognitive impairment, and the like.

The cognitive impairment diagnosis system according to the embodiments may analyze the electroencephalogram signal generated by the electroencephalogram measurement device 200 in the cognitive impairment diagnosis device 100 and provide the determined degree of the cognitive impairment of the user through the user terminal 300. The cognitive impairment diagnosis device 100 may transmit, to another server external thereto, data about the diagnosed degree of the cognitive impairment and/or the diagnosed cause of the cognitive impairment.

The cognitive impairment diagnosis device 100 may provide diagnosis information (the degree of the cognitive impairment, the cause of the cognitive impairment, an improvement effect of the cognitive impairment, whether dementia is present, and the like) and allow subsequent monetary payments to be made. The cognitive impairment diagnosis device 100 may differentially determine the amount of money to be paid according to aims, capacity, importance, and the like of the provided diagnosis information.

The cognitive impairment diagnosis device 100 may early detect MCI using biomarkers selected by the cognitive impairment diagnosis model. The cognitive impairment diagnosis device 100 may extract biomarkers for cognitive impairment diagnosis and prediction from pathophysiological characteristics to determine the cause of the cognitive impairment. The cognitive impairment diagnosis device 100 may recommend a drug capable of enhancing the improvement effect of the cognitive impairment using the pathophysiological characteristics of the user. The cognitive impairment diagnosis device 100 may determine causes of cognitive impairments to group and/or classify users with cognitive impairments in detail, thereby efficiently performing treatment for a cognitive impairment of a user. The cognitive impairment diagnosis device 100 may perform periodic measurements and diagnoses of cognitive impairments for each group to perform improvements on diseases such as cognitive impairments and the like. The cognitive impairment diagnosis device 100 may quickly and efficiently determine a dementia-related drug subject group by selecting cognitive impairment patients at an early stage that is difficult to diagnose, using the cognitive impairment diagnosis model.

Figure 2:
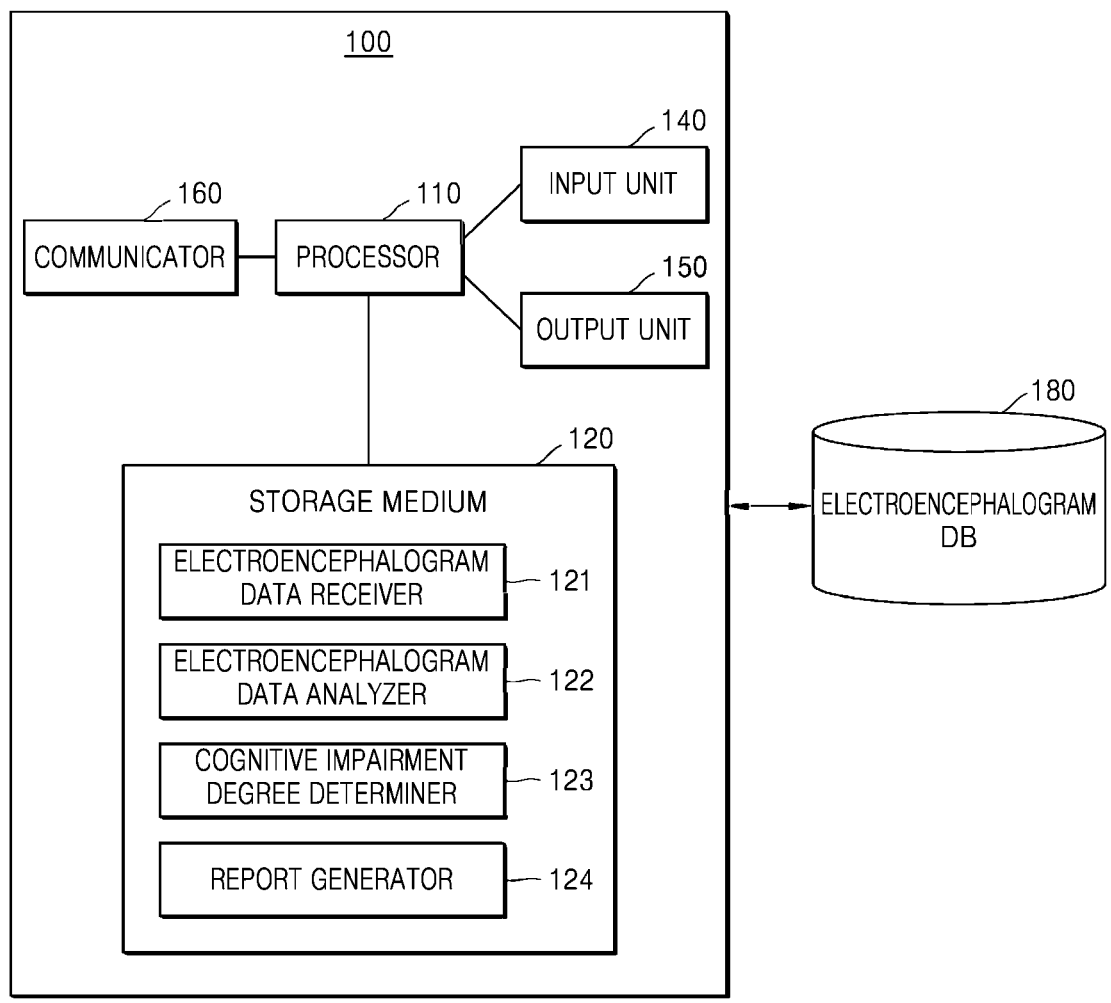
FIG. 2 is a block diagram of a cognitive impairment diagnosis device according to embodiments.

FIG. 2 is a block diagram of the cognitive impairment diagnosis device 100, according to embodiments.

The cognitive impairment diagnosis device 100 may include a processor 110, a storage medium 120, an input unit 140, an output unit 140, a communicator 160, and an electroencephalogram database 180.

The processor 110 may be included as one or more processors. The processor 110 usually controls an overall operation of the cognitive impairment diagnosis device 100. For example, the processor 110 may overall control the input unit 140, the output unit 150, the communicator 160, and the like by executing programs stored in the storage medium 120.

The storage medium 120 may store programs for processing and controlling of the processor 110 and may also store pieces of input/output data.

The storage medium 120 may include at least one type of storage medium selected from a flash memory type, a hard disk type, a multimedia card micro type, a card type of memory (e.g., SD or XD memory or the like), random access memory (RAM), static random access memory (SRAM), read-only memory (ROM), electrically erasable programmable read-only memory (EEPROM), programmable read-only memory (PROM), magnetic memory, a magnetic disk, and an optical disk. Also, the cognitive impairment diagnosis device 100 may operate a web storage or a cloud server that performs a storage function of the storage medium 120 on the Internet. The programs stored in the storage medium 120 may be classified into a plurality of modules according to functions thereof. The storage medium 120 may further include various types of modules related to a system, an OS, and hardware of the cognitive impairment diagnosis device 100.

The input unit 140 refers to a means through which a user inputs data for controlling an electronic device. For example, the input unit 140 may be a keypad, a dome switch, a touch pad (a contact capacitive type, a pressure resistive film type, an infrared detection type, a surface ultrasonic conduction type, an integral tension measurement type, a piezoelectric effect type, or the like), a jog wheel, a jog switch, or the like but is not limited thereto.

The output unit 150 outputs information processed by the cognitive impairment diagnosis device 100. For example, the output unit 150 may output information about electroencephalogram signals input in various ways, such as visual and auditory ways and the like, and information about determined degrees of cognitive impairments. The output unit 150 may output a user interface provided by executing the programs stored in the storage medium 120.

The communicator 160 may include one or more components that enable communication between the cognitive impairment diagnosis device 100 and another electronic device, a server, or the like external thereto.

The storage medium 120 may include an electroencephalogram data receiver 121, an electroencephalogram data analyzer 122, a cognitive impairment degree determiner 123, and a report generator 124 to determine a degree of a cognitive impairment and/or a cause of the cognitive impairment, and the like from an electroencephalogram signal of a user.

The electroencephalogram data receiver 121 receives the electroencephalogram signal from an electroencephalogram measurement device.

The electroencephalogram data analyzer 122 analyzes the electroencephalogram signal. The electroencephalogram data analyzer 122 may preprocess the electroencephalogram signal to easily analyze the electroencephalogram signal. The electroencephalogram data analyzer 122 may amplify the electroencephalogram signal and frequency-filter the amplified electroencephalogram signal to remove noise included in the electroencephalogram signal. The cognitive impairment degree determiner 123 may determine the degree of the cognitive impairment, the cause of the cognitive impairment, and the like by analyzing the electroencephalogram signal. The cognitive impairment degree determiner 123 may determine the degree of the cognitive impairment, the cause of the cognitive impairment, and the like using a cognitive impairment diagnosis model.

The electroencephalogram data analyzer 122 may estimate, from the electroencephalogram signal, a degree of atrophy of each part of cerebral cortex and/or a degree of ischemic damage of cerebral white matter. The electroencephalogram data analyzer 122 may extract, from the electroencephalogram signal, statistical comparison values with normal persons of the same age for a current concentration in each frequency band, absolute power or relative power, ratios and coupling between frequency bands, and the like in a cortical area, using absolute power and relative power of a power spectrum of an electroencephalogram, the magnitude of each frequency component of the power spectrum of the electroencephalogram, an alpha peak frequency of the electroencephalogram, ratios and coupling between different frequency bands of the electroencephalogram, connectivity of each position of the electroencephalogram, complexity of the electroencephalogram, or various techniques (inverse problem solutions) reconstructing an electrical signal source in a brain. The electroencephalogram data analyzer 122 may extract features to use, as major markers, whether major sources of an electroencephalogram in the scalp and an electroencephalogram signal in the cortical area are abnormal, local connectivity intensity between major areas in the brain, overall connectivity intensity between the major areas, complexity, synchronicity, and the like. The electroencephalogram data analyzer 122 may determine the degree of the cognitive impairment and the cause of the cognitive impairment for the electroencephalogram signal using the cognitive impairment diagnosis model.

The electroencephalogram data analyzer 122 may extract the features included in the electroencephalogram signal and determine the degree of the cognitive impairment and the cause of the cognitive impairment on the basis of features selected from the extracted features through the cognitive impairment diagnosis model. The electroencephalogram data analyzer 122 may select, through the cognitive impairment diagnosis model, the feature related to whether a mild cognitive impairment occurs and the feature related to a possibility of a cognitive impairment that may develop into a significant cognitive impairment. In detail, the electroencephalogram data analyzer 122 may infer a degree of atrophy of each part of cerebral cortex and/or a degree of ischemic damage of cerebral white matter of a user or an object, using at least one selected from the current concentration in each frequency band, the absolute power or the relative power, the ratios between the frequency bands, and the statistical comparison values with the normal persons of the same age. For example, the electroencephalogram data analyzer 122 may determine the cause of the cognitive impairment as a neurodegenerative cognitive impairment disease when the degree of atrophy of each part of the cerebral cortex is greater than the degree of ischemic damage of the cerebral white matter and determine the cause of the cognitive impairment as vascular dementia when the degree of atrophy of each part of the cerebral cortex is less than the degree of ischemic damage of the cerebral white matter. Alternatively, the electroencephalogram data analyzer 122 may use the cognitive impairment diagnosis model to select a feature (e.g., the degree of atrophy of each part of the cerebral cortex) related to whether the cause of the cognitive impairment is neurodegenerative (e.g., Alzheimer's disease) and a feature (e.g., the degree of ischemic damage of the cerebral white matter) related to whether the cause of the cognitive impairment is vascular.

The electroencephalogram data analyzer 122 may determine anatomical position information of the brain in which abnormality in neuroactivity is observed, on the basis of features (e.g., the current concentration in each frequency band, the absolute power or the relative power, the ratios between the frequency bands, complexity, and the like) related to whether neuroactivity of a brain cortex is abnormal. The current concentration in each frequency band refers to power in each frequency band and refers to one of absolute power and relative power. The absolute power may be calculated by performing Fourier Transform to calculate power in each frequency band and sum the power in each frequency band. The relative power may be set by using the total power as a denominator and the power of each frequency band as a numerator. The complexity refers to the unpredictability of a signal and may be output as a single number.

The report generator 124 may generate a report related to determined cognitive impairment diagnosis and prediction. The report generator 124 may generate the report including results of the degree of the cognitive impairment, whether neurodegenerative dementia occurs, whether vascular dementia occurs, and the like. The report generator 124 synthesizes the analyzed results to generate diagnosis information about the cognitive impairment and a dementia symptom of the user. The report generator 124 may use the features selected through the cognitive impairment diagnosis model to generate cognitive impairment diagnosis information including the degree of the cognitive impairment, the cause of the cognitive impairment, and the like of the user.

The cognitive impairment diagnosis device 100 may transmit, to the electroencephalogram database 180, the electroencephalogram signal and data about cognitive impairment diagnosis and prediction and the like.

The electroencephalogram database 180 may manage the cognitive impairment diagnosis model and data for generating the cognitive impairment diagnosis model. The electroencephalogram database 180 may store and manage pieces of measured electroencephalogram data in association with information about the object. The electroencephalogram database 180 may manage the measured electroencephalogram data and diagnosis data corresponding to the measured electroencephalogram data in association with each other. The electroencephalogram database 180 may manage whether the cognitive impairment occurs, the degree of the cognitive impairment, the cause of the cognitive impairment, and the like in association with the measured electroencephalogram data or feature values of the measured electroencephalogram data. The electroencephalogram database 180 may manage treatment methods, treatment drugs, lifestyle habits (smoking-related information, drinking-related information, sleep time, and the like), environment information (genetic histories of parents, occupation, residential information, and the like), and the like that are classified on the basis of whether the cognitive impairment occurs, the degree of the cognitive impairment (degree of progression, severity, and the like), and/or the cause of the cognitive impairment. A treatment method, a treatment drug, a lifestyle habit, environment information, and the like suitable for a patient with a degree of a first cognitive impairment may be stored. Also, according to personal information of the patient, a treatment method, a treatment drug, a lifestyle habit, environment information, and the like may be classified and stored.

Therefore, the cognitive impairment diagnosis device 100 according to the embodiments may accurately diagnose a degree of a cognitive impairment using an electroencephalogram signal of a user. The cognitive impairment diagnosis device 100 may use the electroencephalogram signal to output cognitive impairment diagnosis information including whether a mild cognitive impairment of the user occurs, a possibility of the cognitive impairment that may develop into a significant cognitive impairment in the future, and the like. The cognitive impairment diagnosis device 100 may diagnose a degree of the cognitive impairment that is not diagnosed by the eyes, a brain image, or the like. Also, the cognitive impairment diagnosis device 100 according to the embodiments may diagnose the cause of the cognitive impairment as one of vascular and neurodegenerative causes of the cognitive impairment, using the electroencephalogram signal of the user.

Figure 3:
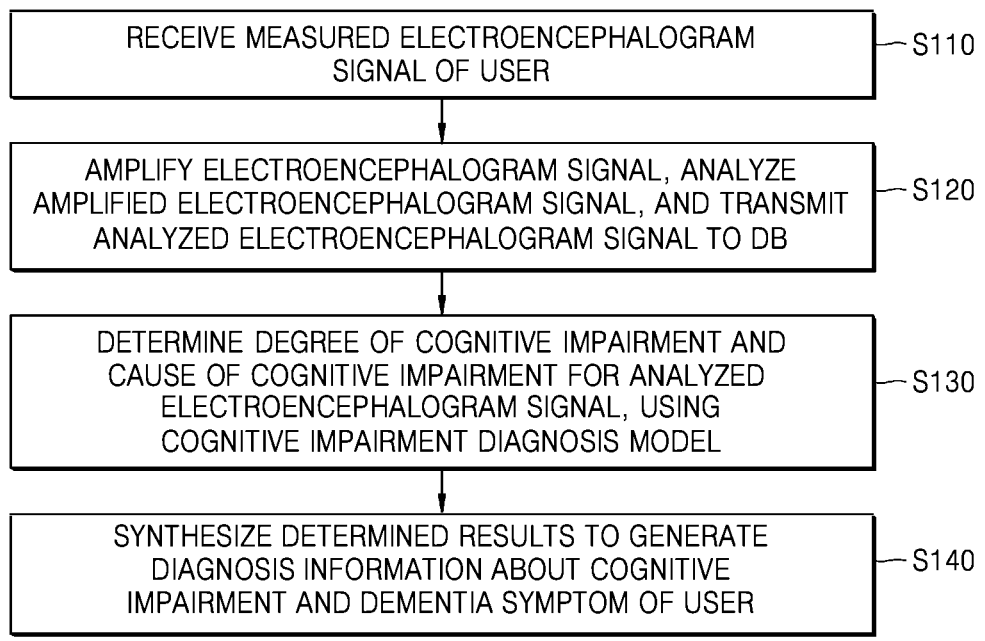
FIG. 3 is a flowchart of a cognitive impairment diagnosis method according to embodiments.

FIG. 3 is a flowchart of a cognitive impairment diagnosis method according to embodiments.

In operation S110, the cognitive impairment diagnosis device 100 receives an electroencephalogram signal of a user.

In operation S120, the cognitive impairment diagnosis device 100 analyzes the electroencephalogram signal. The cognitive impairment diagnosis device 100 amplifies the electroencephalogram signal and analyzes the amplified electroencephalogram signal. The cognitive impairment diagnosis device 100 transmits the analyzed electroencephalogram signal to a database. The cognitive impairment diagnosis device 100 may analyze the electroencephalogram signal using a statistical or mathematical and physical method. The cognitive impairment diagnosis device 100 may estimate, from the electroencephalogram signal, a degree of atrophy of each part of cerebral cortex and/or a degree of ischemic damage of cerebral white matter. The cognitive impairment diagnosis device 100 may extract, from the electroencephalogram signal, statistical comparison values with normal persons of the same age and the like for a current concentration in each frequency band, absolute power or relative power, ratios and coupling between frequency bands, and the like in a cortical area, using various techniques (inverse problem solutions) reconstructing absolute power and relative power of a power spectrum of an electroencephalogram, the magnitude of each frequency component of the power spectrum of the electroencephalogram, an alpha peak frequency of the electroencephalogram, ratios and coupling between different frequency bands of the electroencephalogram, connectivity of each position of the electroencephalogram, complexity of the electroencephalogram, or an electrical signal source in a brain. The cognitive impairment diagnosis device 100 may extract features to use, as major markers, whether major sources of an electroencephalogram signal in the scalp and an electroencephalogram signal in the cortex area are abnormal, local connectivity intensity between major areas in the brain, overall connectivity intensity between the major areas, complexity, synchronicity, and the like.

In operation S130, the cognitive impairment diagnosis device 100 determines a degree of a cognitive impairment and a cause of the cognitive impairment for the electroencephalogram signal analyzed using a cognitive impairment diagnosis model. The cognitive impairment diagnosis device 100 may extract the features included in the electroencephalogram signal and determine the degree of the cognitive impairment and the cause of the cognitive impairment on the basis of the features selected from the extracted features through the cognitive impairment diagnosis model. The cognitive impairment diagnosis device 100 may select, through the cognitive impairment diagnosis model, the feature related to whether a mild cognitive impairment occurs and the feature related to a possibility of the cognitive impairment that may develop into a significant cognitive impairment. In detail, the cognitive impairment diagnosis device 100 may infer a degree of atrophy of each part of cerebral cortex and/or a degree of ischemic damage of cerebral white matter of a user or an object, using at least one selected from the current concentration in each frequency band, the absolute power or the relative power, the ratios between the frequency bands, and the statistical comparison values with the normal persons of the same age. For example, the cognitive impairment diagnosis device 100 may determine the cause of the cognitive impairment as a neurodegenerative cognitive impairment disease when the degree of atrophy of each part of the cerebral cortex is greater than the degree of ischemic damage of the cerebral white matter and determine the cause of the cognitive impairment as vascular dementia when the degree of atrophy of each part of the cerebral cortex is less than the degree of ischemic damage of the cerebral white matter. Alternatively, the cognitive impairment diagnosis device 100 may use the cognitive impairment diagnosis model to select the feature (e.g., the degree of atrophy of each part of the cerebral cortex) related to when the cause of the cognitive impairment is neurodegenerative (e.g., Alzheimer's disease) and the feature (e.g., the degree of ischemic damage of the cerebral white matter) related to whether the cause of the cognitive impairment is vascular.

In another embodiment, the cognitive impairment diagnosis device 100 may determine anatomical position information of the brain in which abnormality in neuroactivity is observed, on the basis of the features (e.g., the current concentration in each frequency band, the absolute power or the relative power, the ratios between the frequency bands, complexity, and the like) related to whether the neuroactivity of a brain cortex is abnormal.

The current concentration in each frequency refers to power in each frequency band and refers to one of absolute power and relative power. The absolute power may be calculated by performing Fourier Transform to calculate the power in each frequency band and sum the power in each frequency band. The relative power may be set by using the total power as a denominator and the power in each frequency band as a numerator.

The complexity refers to unpredictability of a signal and may be output as a single number.

Whether these features are abnormal may be determined by comparing the features with normative values of corresponding features acquired from a normal group. When statistically significant differences appear in comparison with the features acquired from the normal persons of the same age, a cognitive impairment may be determined as occurring in the user. Alternatively, information related to the cognitive impairment of the user may be determined using a model that machine-learns features acquired from electroencephalogram signals of a comparison group with respective diseases such as a Alzheimer's type of mild cognitive impairment, a Lewy body dementia type of mild cognitive impairment, a vascular dementia type of mild cognitive impairment, and the like.

For example, a degree of a cognitive impairment may be determined as abnormal findings of a mild stage or a moderate or higher stage by comparing normative values of features with a preset value. For example, if the normative values of the features are smaller than or equal to 1.5 z-score or 16 percentile, the degree of the cognitive impairment may be determined as the abnormal findings of the mild stage, and if the normative values of the features are smaller than or equal to 2 z-score or 7 percentile, the degree of the cognitive impairment may be determined as the abnormal findings of the moderate or higher stage. Therefore, the cognitive impairment diagnosis device 100 may determine the position information in which the abnormality in the neuroactivity is observed as one of the temporal lobe, the occipital lobe, the parietal lobe, and the frontal lobe and determine the cause of the cognitive impairment and/or prognosis estimation information of the cognitive impairment on the basis of a position in which abnormality is observed. The cognitive impairment diagnosis device 100 may determine the degree of the cognitive impairment according to the position in which the abnormality is observed. For example, the degree of the cognitive impairment may be determined as a mild memory loss type of mild cognitive impairment even when the position in which the abnormality is observed is the temporal lobe, as Alzheimer's early stage when the position in which the abnormality is observed includes the parietal lobe or the occipital lobe, as Alzheimer's middle or more stage when the position in which the abnormality is observed is all of the temporal lobe, the parietal lobe, and frontal lobe, and as frontotemporal dementia or Lewy body dementia when abnormal findings are not observed in the temporal lobe or the parietal lobe but are mainly observed in the frontal lobe.

In operation S140, the cognitive impairment diagnosis device 100 synthesizes the analyzed results to generate diagnosis information about the cognitive impairment and a dementia symptom of the user. The cognitive impairment diagnosis device 100 may generate cognitive impairment diagnosis information including the degree of the cognitive impairment and the cause of the cognitive impairment, using the features selected through the cognitive impairment diagnosis model. The cognitive impairment diagnosis device 100 may generate the generated cognitive impairment diagnosis information as a single report.

Figure 4:
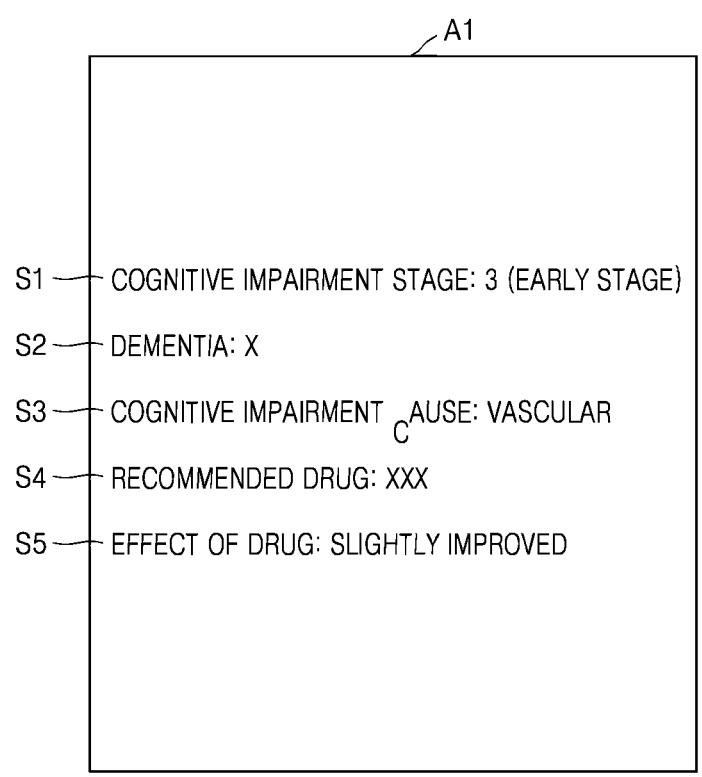
FIG. 4 is an example view of a report generated through a cognitive impairment diagnosis device.

FIG. 4 is an example view of a report generated through the cognitive impairment diagnosis device 100.

A report A1 generated through the cognitive impairment diagnosis device 100 may provide cognitive impairment stage information S1, dementia information S2, cognitive impairment cause information S3, recommended drug information S4, and drug effect information S5. The drug effect information S5 may vary according to a state of each user. For example, the drug effect information S5 may include normal information about the recommended drug before a drug is injected into a user but, after the drug is injected into the user, may include an effect of the injected drug through a process of searching for the drug injected into the user and comparing a degree of a cognitive impairment after injecting the drug with a degree of the cognitive impairment before injecting the drug.

Figure 5:
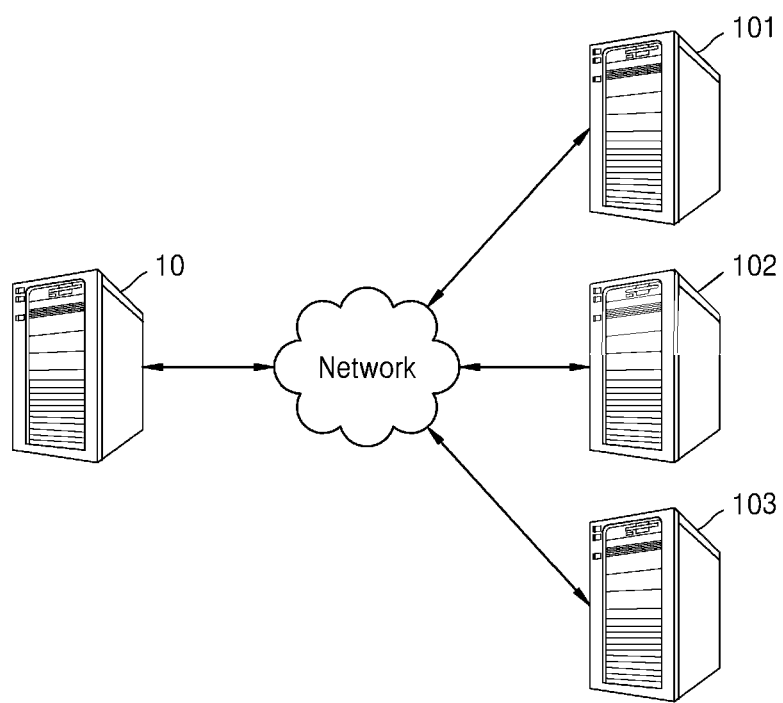
FIG. 5 is a view of a modeling system of a cognitive impairment diagnosis model.
Figure 6:
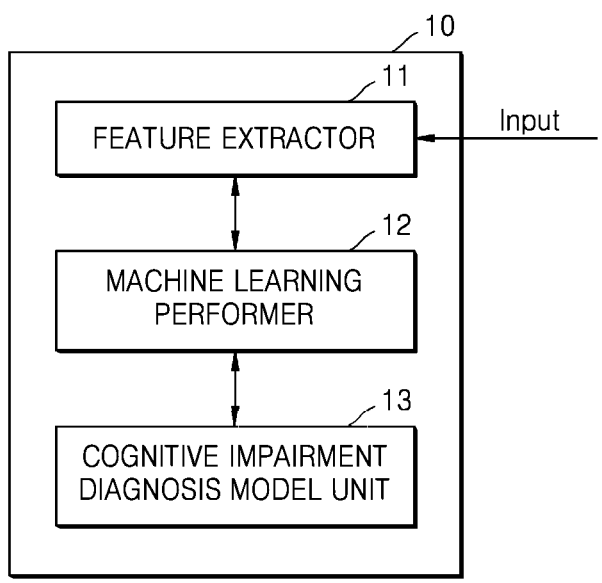
FIG. 6 is a block diagram of a modeling device.

FIG. 5 is a view of a modeling system of a cognitive impairment diagnosis model.

As shown in FIG. 5, the modeling system of the cognitive impairment diagnosis model may include a modeling device 10 and a plurality of cognitive impairment diagnosis devices 101, 102, and 103.

The modeling device 10 may train a cognitive impairment diagnosis model by receiving an electroencephalogram signal, a brain image, diagnostician's opinions, question and answer data, and/or diagnosis information (a degree of a cognitive impairment, a cause of the cognitive impairment, and the like) through the plurality of cognitive impairment diagnosis devices 101, 102, and 103. The modeling device 10 may include an additional input/output device to receive and learn the electroencephalogram signal, the brain image, the diagnostician's opinions, the question and answer data, and/or the diagnosis information (the degree of the cognitive impairment, the cause of the cognitive impairment, and the like) through an input/output device through which information is input by a specialist or the like. Here, the modeling device 10 may be embodied to evaluate input data and receive an input of merely qualitatively superior data. Whether the input data is the qualitatively superior data may be determined using a test on an input user. Whether the input data is the qualitatively superior data may be determined on the basis of evaluation data about a model trained merely with pieces of data previously input through the user input. When the evaluation data is evaluated above a preset reference score, the input data may be evaluated as qualitatively superior data. The modeling device 100 may transmit the trained and updated cognitive impairment diagnosis model to the plurality of cognitive impairment diagnosis devices 101, 102, and 103. The plurality of cognitive impairment diagnosis devices 101, 102, and 103 may have structures and functions that are the same as or similar to the cognitive impairment diagnosis device 100 of FIG. 1.

The modeling device 10 may include a feature extractor 11, a machine learning performer 12, and a cognitive impairment diagnosis model unit 13. The modeling device 10 may be a computing device including one or more processors. The modeling device 10 may receive input data through the plurality of cognitive impairment diagnosis devices 101, 102, and 103 or may receive an input of input data through a provided input device. The cognitive impairment diagnosis model generated through the modeling device 10 may be transmitted to each of the plurality of cognitive impairment diagnosis devices 101, 102, and 103 to update the cognitive impairment diagnosis devices 101, 102, and 103. The modeling device 10 may further include a learning algorithm for learning. The learning algorithm may be received from an external server and updated.

The feature extractor 11 may extract one or more features by analyzing the electroencephalogram signal, the brain image, the diagnostician's opinions, the question and answer data, and the like that are input. The feature extractor 11 may extract, from the electroencephalogram signal, statistical comparison values with normal persons of the same age for a current concentration in each frequency band, absolute power or relative power, ratios between frequency bands, and the like, using various techniques reconstructing absolute power and relative power of a power spectrum of an electroencephalogram, the magnitude of each frequency component of the power spectrum of the electroencephalogram, an alpha peak frequency of the electroencephalogram, ratios and coupling between different frequency bands of the electroencephalogram, connectivity of each position of a ring electroencephalogram, complexity of the electroencephalogram, or an electrical signal source in a brain.

The machine learning performer 12 learns, as a set, output data including the electroencephalogram signal, the brain image, the diagnostician's opinions, the question and answer data, the degree of the cognitive impairment, the cause of the cognitive impairment, and the like that are input. The machine learning performer 12 may learn through a process of extracting features included in the electroencephalogram signal, the brain image, the diagnostician's opinions, and the question and answer data that are input and classifying the features included in the electroencephalogram signal according to the output data. The machine learning performer 12 extracts, through learning, features related to a degree of atrophy of each part of cerebral cortex and features related to a degree of ischemic damage of cerebral white matter. The machine learning performer 12 may learn the input data and result information related to the cognitive impairment using a neural network imitating a human brain function. The machine learning performer 12 may learn, through repetitive input data, relationships between the electroencephalogram signal and the degree of the cognitive impairment and between the electroencephalogram signal and the cause of the cognitive impairment. Classifying electroencephalogram signals that are input data according to the degree of the cognitive impairment and the cause of the cognitive impairment that are output data may be connecting of one or more factors included in the input data to pieces of the output data One or more factors included in the electroencephalogram signal, the brain image, the diagnostician's opinions, the question and answer data, and the like that are input data may have a causal relationship with hidden data to be finally inferred as pieces of output data related to the cognitive impairment. Factors included in the input data may be connected to the hidden data on the basis of a causal relationship inferred by machine learning. Here, the hidden data is not included in the electroencephalogram signal that is the input data or cognitive impairment-related information that is the output data but refers to features, characteristics, attributes, factors, or data used in an inference process from the electroencephalogram signal to the cognitive impairment-related information. The output data corresponding to the input data may be learned using a connection between at least two selected from the input data, the hidden data, and the output data. According to the present embodiment, the input data is the electroencephalogram signal and may be a gamma ($\gamma$) wave, an alpha ($\alpha$) wave, a beta ($\beta$) wave, a delta ($\delta$) wave, a theta ($\theta$) wave, or the like acquired through various types of electroencephalogram measurement devices, in detail, measured through a plurality of channels. The output data may be the degree of the cognitive impairment, the cause of the cognitive impairment, or the like of the user. The input data may further include the electroencephalogram signal, the brain image, the diagnostician's opinions, the question and answer data, and the like. Detailed structure and operation of the machine learning performer 12 will be further described in detail with reference to FIGS. 13 and 14.

The modeling device 10 may be continuously trained according to the electroencephalogram signal and the degree of the cognitive impairment acquired from one or more of the cognitive impairment diagnosis devices 101, 102, and 103. As the amount of data that is input increases, prediction accuracy of the degree of the cognitive impairment and the cause of the cognitive impairment of the user according to the electroencephalogram signal may increase. The modeling device 10 may periodically transmit the updated cognitive impairment diagnosis model to the cognitive impairment diagnosis devices 101, 102, and 103.

The degree of the cognitive impairment and the cause of the cognitive impairment of the user output by one or more of the cognitive impairment diagnosis devices 101, 102, and 103 may be determined as one or more result values. For each of the determined result values, each matching probability may be further included. For example, the degree of the cognitive impairment may be output as a first cognitive impairment and a second cognitive impairment, and probabilities of the first cognitive impairment and the second cognitive impairment may be inferred and output as 7 to 3.

The cognitive impairment diagnosis model unit 13 models the cognitive impairment diagnosis model using the results learned through the machine learning performer 12. The cognitive impairment diagnosis model may use the electroencephalogram signal as an input and output the degree of the cognitive impairment and the cause of the cognitive impairment using the features extracted from the electroencephalogram signal.

The cognitive impairment diagnosis model unit 13 may be embodied to diagnose pieces of complex information at once in association with a diagnosis of the cognitive impairment. For example, the cognitive impairment diagnosis model unit 13 may generate a multidimensional model function that generates each of the degree of the cognitive impairment and the cause of the cognitive impairment on one axis. The cause of the cognitive impairment may be vascular dementia, degenerative dementia, or the like. As output values (cognitive impairment-related information) output through the electroencephalogram signal increase, an axis of a model function increases.

Figure 8:
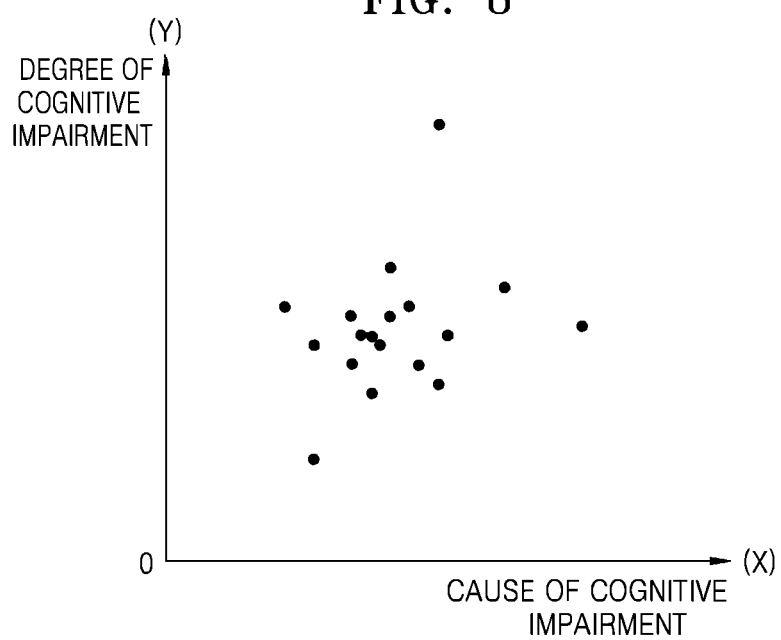
FIG. 8 is one example view for a cognitive impairment diagnosis model in a three-dimensional space.

As shown in FIG. 8, a cognitive impairment diagnosis model determines a dimension of modeling on the basis of information output as a result of prediction in relation to a cognitive impairment. For example, when the cognitive impairment diagnosis model outputs two types of cognitive impairment diagnosis information, such as a degree of the cognitive impairment and a cause of the cognitive impairment, among cognitive impairment-related result values using features extracted on the basis of an electroencephalogram signal, the cognitive impairment diagnosis model may be modeled to include two axes of the degree of the cognitive impairment and the cause of the cognitive impairment.

Figure 9:
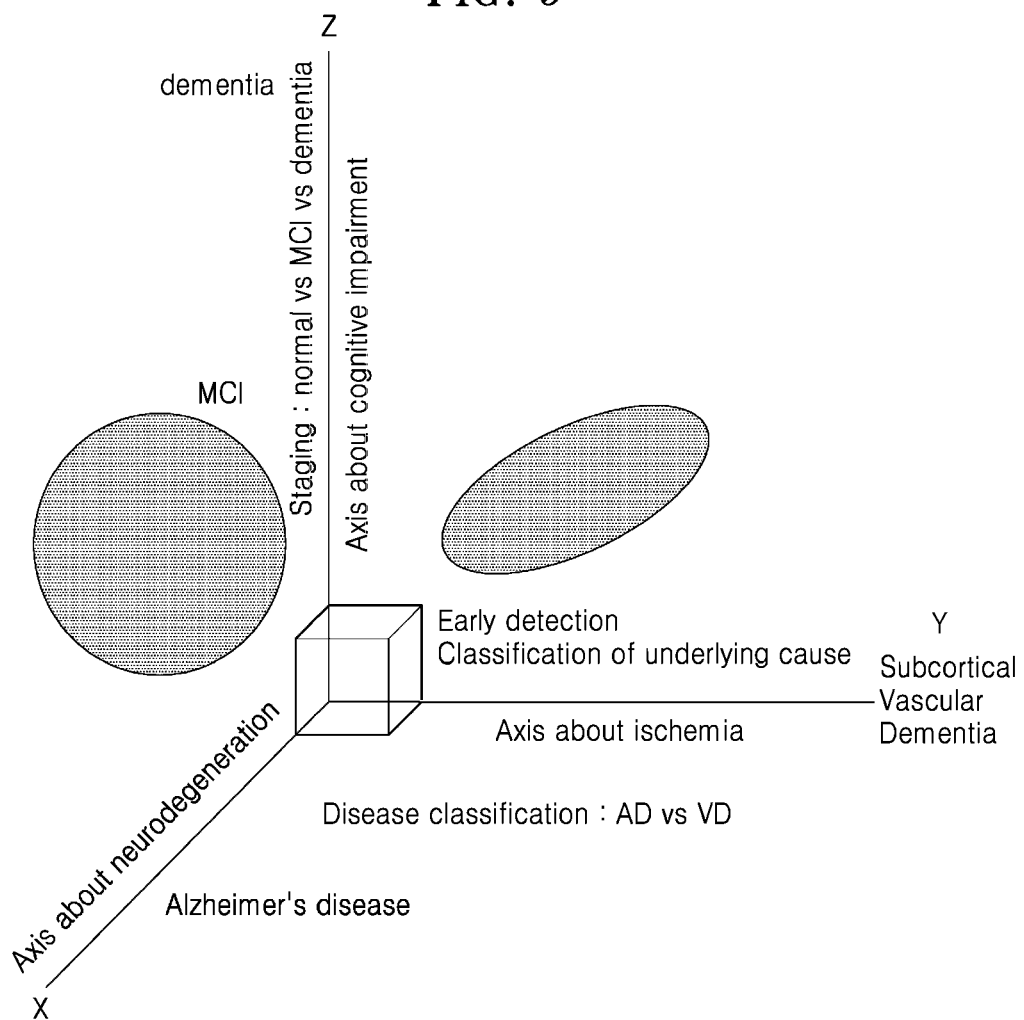
FIG. 9 is another example view for a cognitive impairment diagnosis model.

As the number of pieces of output data that is inferred cognitive impairment-related information increases, a dimension of the cognitive impairment diagnosis model may increase to three dimensions with three axes. In detail, as types of the cause of the cognitive impairment belonging to result values of the cognitive impairment diagnosis model increase, the cognitive impairment diagnosis model may be automatically modeled to include axes respectively corresponding to the types of the cause of the cognitive impairment output as results. As shown in FIG. 9, when a type of a cause of a cognitive impairment is classified and output as a vascular or degenerative type, a cognitive impairment diagnosis model may be three-dimensionally designed so that result values of causes of the cognitive impairment output by the cognitive impairment diagnosis model are respectively inferred. Also, when causative diseases such as Lewy body dementia, frontotemporal dementia, and the like are added, output dimensions of the result values may increase.

The cognitive impairment diagnosis model outputs output data such as a degree of the cognitive impairment, the cause of the cognitive impairment, and the like in a multidimensional modeling method, with respect to an electroencephalogram signal that is an input. As a result of machine learning in the cognitive impairment diagnosis model, one or more pieces of output data may be output, and each piece of the output data may have a probability value.

As shown in FIG. 9, in a three-dimensional space, output data for first input data may be displayed as a preset area. According to the probability values, respective points in the displayed area may be expressed in a way of being distinguished from one another.

Figure 7:
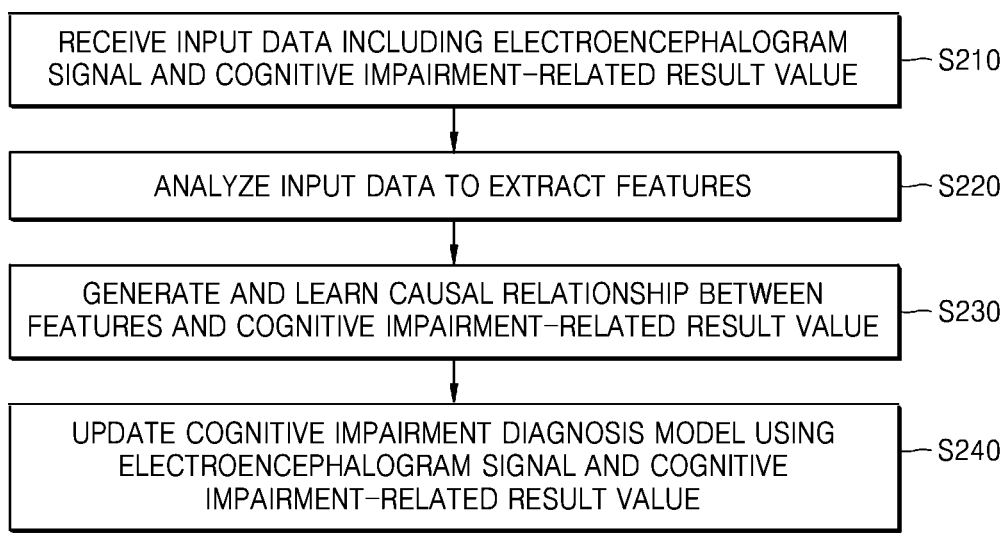
FIG. 7 is a flowchart of a cognitive impairment diagnosis modeling method according to embodiments.

FIG. 7 is a flowchart of a cognitive impairment diagnosis modeling method according to embodiments.

The cognitive impairment diagnosis modeling method generates an electroencephalogram (EEG)-based distinguishing model for distinguishing a healthy elderly person from dementia or a mild cognitive impairment (MCI). The cognitive impairment diagnosis modeling method generates an EEG-based model for a major pathophysiological degeneration evaluation for neurodegenerative changes and ischemic damage. Here, MRI white matter intensity and MRI 3D volume analysis results (such as information related to hippocampal atrophy, cortical lobe atrophy, and the like) may be used.

The cognitive impairment diagnosis modeling method may generate an electroencephalogram-based distinguishing model for distinguishing neurodegenerative dementia (AD, Alzheimer's type dementia) from (VD, vascular dementia).

A cognitive impairment diagnosis model may extract electroencephalogram markers that may reflect a degree of atrophy of each part of cerebral cortex. The cognitive impairment diagnosis model may extract a current concentration in each frequency band, absolute or relative power, ratios between frequency bands, statistical comparison values acquired through comparisons of normative values with normal persons of the same age, and the like, for electrical signals in a brain calculated using absolute power and relative power of a power spectrum of an electroencephalogram, the magnitude of each frequency component of the power spectrum of the electroencephalogram, an alpha peak frequency of the electroencephalogram, ratios and coupling between different frequency bands of the electroencephalogram, connectivity of each position of a ring electroencephalogram, complexity of the electroencephalogram, or various techniques (referred to as inverse problem solutions) reconstructing an electrical signal source in the brain on the basis of the electroencephalogram measured in scalp. Also, the cognitive impairment diagnosis model may extract electroencephalogram markers for estimating a degree of ischemic damage of cerebral white matter. For the electrical signals in the brain calculated using the various techniques reconstructing the electrical signal source in the brain on the basis of the electroencephalogram measured in the scalp, the cognitive impairment diagnosis model may extract calculated values for connectivity and synchronicity between major areas of the brain, statistical comparison values acquired by comparing the calculated values with the normative values of the normal persons of the same age, and the like. When the electroencephalogram markers reflecting the atrophy of the cerebral cortex is superior to (higher than) the electroencephalogram markers reflecting the ischemic damage of the cerebral white matter, the cognitive impairment diagnosis model may determine a cause of a cognitive impairment as a neurodegenerative disease (representatively, Alzheimer's disease) and as vascular dementia in an opposite case.

The cognitive impairment diagnosis model may include anatomical position information of the brain in which abnormality in neuroactivity of the brain cortex estimated through an inverse problem solution technique is observed. The cognitive impairment diagnosis model may extract, from an electroencephalogram signal, position information in which the abnormality in the neuroactivity is observed, using the current concentration in each frequency band, the absolute or relative power, the ratios between frequency bands, the statistical comparison values with the normal persons of the same age, and the like. In other words, the anatomical position information, such as whether such abnormal findings are limited to temporal lobe including hippocampus, are observed in parietal lobe or occipital lobe, or are observed in (pre-) frontal lobe, may be included as significant variables in cause identification and prognosis estimation. The cognitive impairment diagnosis model may determine a degree of the cognitive impairment according to a position in which abnormality is observed. For example, the degree of the cognitive impairment may be determined as a mild memory loss type of mild cognitive impairment when the position in which the abnormality is observed is the temporal lobe, as Alzheimer's early stage when the position in which the abnormality is observed includes the parietal lobe or the occipital lobe, as Alzheimer's middle or more stage when the position in which the abnormality is observed is all of the temporal lobe, the parietal lobe, the occipital lobe, and the frontal lobe, and as frontotemporal dementia or Lewy body dementia when the abnormality is not observed in the temporal lobe or the parietal lobe but abnormal findings are observed mainly in the frontal lobe. Also, the connectivity between the major areas of the brain may differentiate a degree of ischemic damage of cerebral white matter according to a phase relation (coherence or correlation) or a relative difference in entropy-based information transmission amount or through a comparison of this numerical value with the normative values of the normal persons.

The cognitive impairment diagnosis modeling method generates an EEG-based grading model for an evaluation of nerve resilience with respect to neurocognitive reserve.

In operation S210, the modeling device 10 receives, for learning, input data including an electroencephalogram signal that is input data and a cognitive impairment-related result value that is output data.

In operation S220, the modeling device 10 analyzes the input data to extract features. The modeling device 10 may analyze the input data to extract features related to cognitive reserve of a user or a nerve resilience-related characteristic. A cognitive reserve model may use, as major markers, whether major sources of an electroencephalogram signal in the scalp and an electroencephalogram signal in a cortical area are abnormal, local connectivity intensity between major areas in a brain, the total connectivity intensity between the major areas, complexity, synchronicity, and the like and may compare and determine relative superiority and inferiority of the cognitive reserve of the user on the basis of normative values of a healthy person of the same age.

The modeling device 10 may classify the input data according to the features. The modeling device 10 may analyze the input data and extract the features as will be described below with reference to FIGS. 13 and 14.

For example, pathophysiological characteristics may be used as hidden data and may include nerve resilience, neurodegeneration, cortical atrophy, protein misfolding, snaps integrity, snaps activity, vascular damage, mitochondrial metabolic function, oxidative stress, white matter changes, and the like. The pathophysiological characteristics may be extracted by synthesizing a brain image, diagnostician's opinions, question and answer data, and the like.

In operation S230, the modeling device 10 generates and learns a causal relationship between the features and the cognitive impairment-related result value.

In operation S240, the modeling device 10 updates a cognitive impairment diagnosis model using the electroencephalogram signal and the cognitive impairment-related result value. The cognitive impairment diagnosis model may be transmitted to cognitive impairment diagnosis devices and installed. The cognitive impairment diagnosis devices may determine a degree of a cognitive impairment and a cause of the cognitive impairment of the user using a function according to the latest cognitive impairment diagnosis model.

Figure 10:
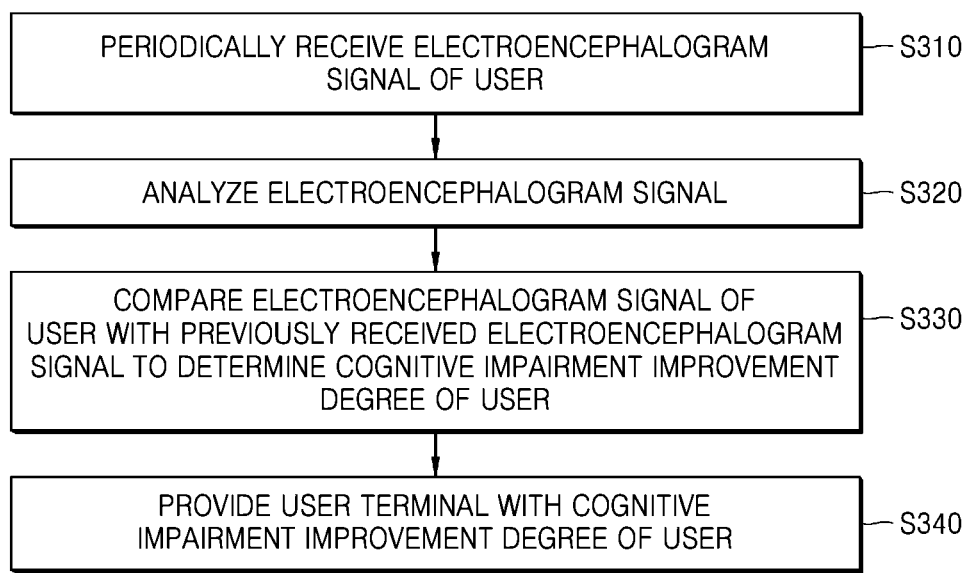
FIG. 10 is a flowchart of an operating method of a cognitive impairment diagnosis device using an electroencephalogram signal of a user.
Figure 11:
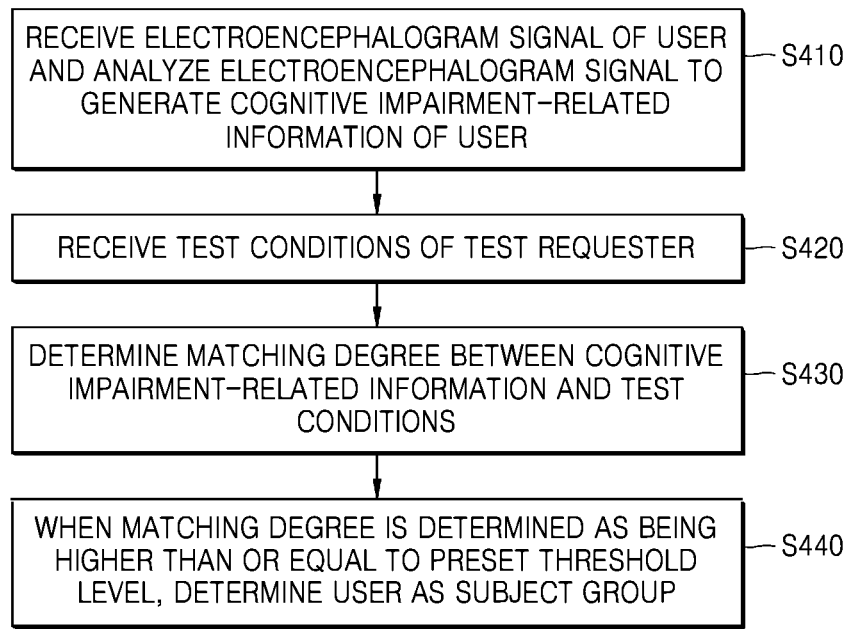
FIG. 11 is a flowchart of an operating method of a cognitive impairment diagnosis device that determines matching degree between cognitive impairment-related information and test conditions.
Figure 12:
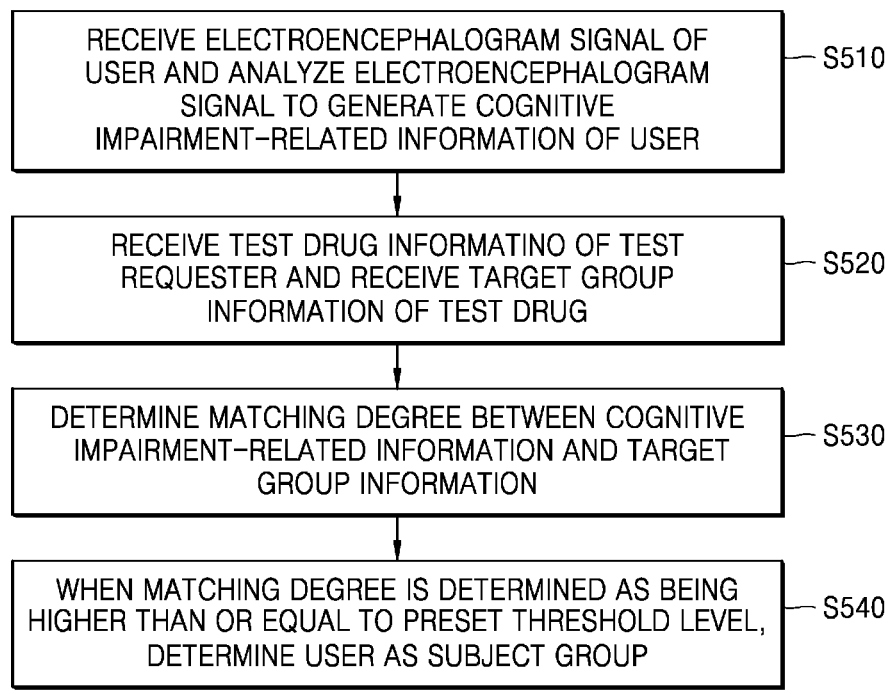
FIG. 12 is a flowchart of an operating method of a cognitive impairment diagnosis device that determines matching degree between cognitive impairment-related information and target information.

FIGS. 10 and 12 are flowcharts of operating methods of a cognitive impairment diagnosis device, according to embodiments.

As shown in FIG. 10, in operation S310, the cognitive impairment diagnosis device 100 receives an electroencephalogram signal of a user. The cognitive impairment diagnosis device 100 receives a measured electroencephalogram signal from the electroencephalogram measurement device 200. In operation S320, the cognitive impairment diagnosis device 100 analyzes the electroencephalogram signal of the user.

In operation S330, the cognitive impairment diagnosis device 100 compares a current electroencephalogram signal with a previously received electroencephalogram signal to determine a cognitive impairment improvement degree of the user. The cognitive impairment diagnosis device 100 may compare the analyzed result with an analyzed result of the previously received electroencephalogram signal to determine the cognitive impairment improvement degree.

In operation S340, the cognitive impairment diagnosis device 100 may provide a user terminal with the cognitive impairment improvement degree of the user. The cognitive impairment improvement degree may be transmitted to various types of servers such as an external insurance company server, a medical institution server, a pharmaceutical company server, and the like. The cognitive impairment improvement degree may be connected to a drug purchased by the user, a treatment procedure, lifestyle habits (exercise, eating habits, a residential environment, other environments, and the like), and the like to be generated in connection with efficacy of the drug, the treatment procedure, the lifestyle habits, and the like.

When the cognitive impairment improvement degree of the user is lower than or equal to a preset smallest improvement value, the cognitive impairment diagnosis device 100 may recommend a new drug, a treatment procedure, a medical institution, a specialist, lifestyle habits, and the like on the basis of cognitive impairment-related information of the user determined through the current electroencephalogram signal. Therefore, the cognitive impairment diagnosis device 100 may objectively calculate an improvement effect of a treatment method even without a brain image or an invasive examination.

In another embodiment, the cognitive impairment diagnosis device 100 may select a subject group of a cognitive impairment-related drug.

In detail, in operation S410, the cognitive impairment diagnosis device 100 may receive an electroencephalogram signal of a user. The cognitive impairment diagnosis device 100 analyzes the electroencephalogram signal to generate cognitive impairment-related information of the user. The cognitive impairment diagnosis device 100 may analyze the electroencephalogram signal by amplifying the electroencephalogram signal to extract features included in the electroencephalogram signal. Alternatively, the cognitive impairment diagnosis device 100 may receive and analyze a brain image, diagnostician's opinions, question and answer data, and the like to generate the cognitive impairment-related information.

In operation S420, the cognitive impairment diagnosis device 100 receives test conditions of a test requester. In operation S430, the cognitive impairment diagnosis device 100 determines a matching degree between the cognitive impairment-related information of the user and the test conditions of the test requester. Whether the test conditions of the test requester are satisfied may be determined on the basis of the cognitive impairment-related information such as a degree of a cognitive impairment of the user, a cause of the cognitive impairment, a period of the cognitive impairment disease, when the cognitive impairment occurs, and the like. Here, the test requester may be a manager of a pharmaceutical company, medical staff of a medical institution, a clinical research officer of a contract research organization, a medical official of a national agency, or the like.

In operation S440, the cognitive impairment diagnosis device 100 determines the user as a subject group when the determined matching degree is determined as being higher than or equal to a preset threshold level.

Therefore, the cognitive impairment diagnosis device 100 may simply determine the subject group in a clinical test for a cognitive impairment-related drug, a treatment method, various medicine and medical supplies such as surgery and the like, and a medical practice. Through the cognitive impairment diagnosis device 100 capable of diagnosing a cognitive impaired person at an early stage, although the cognitive impaired person at the early stage is not a severe cognitive impaired patient, the cognitive impaired person at the early stage may be used in a clinical test for a drug, a treatment procedure, surgery, and the like for an early cognitive impairment. Therefore, the clinical test may be made by subdividing a degree of a cognitive impairment, a cause of the cognitive impairment, a drug to be used, a treatment period, a treatment method, and the like.

After the subject group is selected, a cognitive impairment improvement degree of the user may also be measured through the cognitive impairment diagnosis device 100. A report of test results of a subject in the clinical test may be completed by quickly calculating cognitive impairment improvement degrees of a plurality of users included in the subject group.

As shown in FIG. 12, in operation S510, the cognitive impairment diagnosis device 100 receives an electroencephalogram signal and analyzes the electroencephalogram signal to generate cognitive impairment-related information of a user.

In operation S520, the cognitive impairment diagnosis device 100 receives test drug-related information of a test requester and target group information. The target group information may be transmitted to a particular user. The target group information may include all or part of the cognitive impairment-related information of the user selected by the test requester. For example, the target group information may be generated by analyzing an electroencephalogram signal of a target user.

In operation S530, the cognitive impairment diagnosis device 100 may determine a matching degree between the cognitive impairment-related information and the target group information.

In operation S540, when the matching degree is determined as being higher than or equal to a preset threshold level, the cognitive impairment diagnosis device 100 may determine the user as a subject group.

Figure 13:
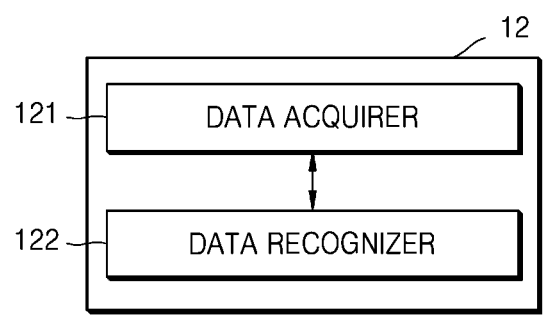
FIG. 13 is a block diagram illustrating a structure of a machine learning performer.
Figure 14:
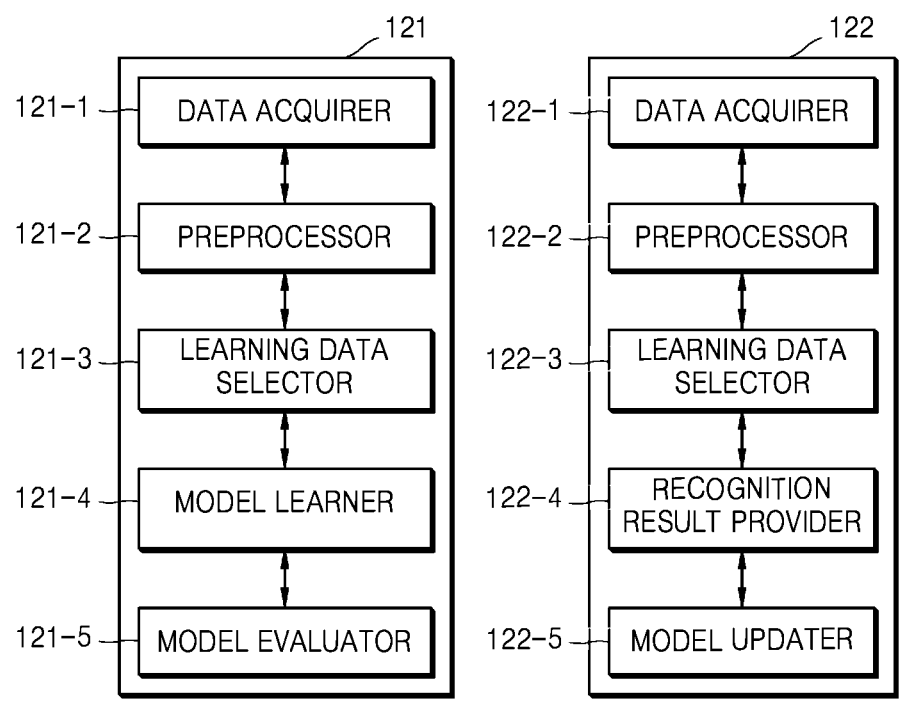
FIG. 14 is a block diagram illustrating structures of a data acquirer and a data recognizer.

FIG. 13 is a block diagram illustrating a structure of the machine learning performer 12. FIG. 14 is a block diagram illustrating structures of a data acquirer 121 and a data recognizer 122.

The machine learning performer 12 may include the data learner 121 and the data recognizer 122. Operations of respective elements will be described as follows.

The data learner 121 may learn criteria for cognitive impairment diagnosis and prediction. The data learner 121 may learn criteria about what data will be used to determine a degree of a preset cognitive impairment and a cause of the preset cognitive impairment and how to determine the degree of the preset cognitive impairment and the cause of the preset cognitive impairment using data. The data learner 121 may be trained to use a multichannel electroencephalogram signal measured with data to be used for learning. Also, the data learner 121 may learn to detect cognitive impairment-related information (the degree of the cognitive impairment, the cause of the cognitive impairment, and the like) using the measured electroencephalogram signal and features included in the electroencephalogram signal. The data learner 121 may output features including connectivity of a brain and effective connectivity, and the like extracted through the electroencephalogram signal.

The data recognizer 122 may detect the cognitive impairment-related information including the degree of the cognitive impairment and the cause of the cognitive impairment of a user on the basis of input data. The data recognizer 122 may detect the cognitive impairment-related information of the user from preset data using a learned cognitive impairment diagnosis model. The data recognizer 122 may acquire the preset data according to criteria preset by learning and use the cognitive impairment diagnosis model using the acquired data as an input value to detect the cognitive impairment-related information of the user on the basis of the preset data. Also, result values output by the cognitive impairment diagnosis model using the acquired data as the input value may be used to update the cognitive impairment diagnosis model.

At least one selected from the data learner 121 and the data recognizer 122 may be manufactured in the form of at least one hardware chip and mounted on an electronic device. For example, at least one selected from the data learner 121 and the data recognizer 122 may be manufactured in the form of a dedicated hardware chip for artificial intelligence (AI) or may be manufactured as part of an existing general-purpose processor (e.g., a CPU or an application processor) or a graphics-only processor (e.g., a GPU) and mounted on various types of electronic devices as mentioned above.

In this case, the data learner 121 and the data recognizer 122 may be mounted on one electronic device or may be respectively mounted on separate electronic devices. For example, one of the data learner 121 and the data recognizer 122 may be included in an electronic device, and the other one may be included in a server. Also, the data learner 121 and the data recognizer 122 may communicate with each other by wire or wireless to provide the data recognizer 122 with model information constructed by the data learner 121 or provide the data learner 121 with data input into the data recognizer 122 as additional learning data.

At least one selected from the data learner 121 and the data recognizer 122 may be embodied as a software module. When at least one selected from the data learner 121 and the data recognizer 122 is embodied as a program module including a software module (or instructions), the software module may be stored in non-transitory computer-readable recording media. Also, in this case, at least one software module may be provided by an operating system (OS) or may be provided by a preset application. Alternatively, part of at least one software module may be provided by an operating system (OS) or may be provided by a preset application.

As shown in FIG. 14, the data learner 121 may include a data acquirer 121-1, a preprocessor 121-2, a learning data selector 121-3, a model learner 121-4, and a model evaluator 121-5.

The data acquirer 121-1 may acquire data needed for cognitive impairment diagnosis and prediction. The data acquirer 121-1 may acquire data needed for learning for the cognitive impairment diagnosis and prediction. The data acquirer 121-1 may acquire an electroencephalogram signal of a user from the electroencephalogram measurement device 200. In detail, the data acquirer 121-1 may acquire a multichannel electroencephalogram signal. The preprocessor 121-2 may preprocess the acquired data to enable the acquired data to be used for learning for the cognitive impairment diagnosis and the prediction. The preprocessor 121-2 may process the acquired data in a preset format to enable the model learner 121-4, which will be described later, to use the data acquired for learning for the cognitive impairment diagnosis and prediction. The preprocessor 121-2 may acquire, from the electroencephalogram signal, features related to a degree of atrophy of each part of cerebral cortex and/or features related to a degree of ischemic damage of cerebral white matter as data. The preprocessor 121-2 may extract, as data, a current concentration in each frequency band, absolute power or relative power, ratios between frequency bands, statistical comparison values with normal persons of the same age, and the like, for electrical signals in a brain. The preprocessor 121-2 may extract, from the electroencephalogram signal, position information in which abnormality in neuroactivity is observed, using the current concentration in each frequency, the absolute or relative power, the ratios between frequency bands, the statistical comparison values with the normal persons of the same age, and the like.

In detail, the preprocessor 121-2 may amplify the electroencephalogram signal. The preprocessor 121-2 may amplify the electroencephalogram signal of the user, filter a frequency domain, and remove noise included in the electroencephalogram signal The preprocessor 121-2 may extract the features of the electroencephalogram signal after filtering and removing noise. The preprocessor 121-2 may extract the features using a brain's connectivity and effective connectivity-based network model. The learning data selector 121-3 may select data needed for learning from the preprocessed data. The selected data may be provided for the model learner 121-4. The learning data selector 121-3 may select the data needed for learning from the preprocessed data according to preset criteria for the cognitive impairment diagnosis and the prediction. Also, the learning data selector 121-3 may select the data according to criteria set by learning by the model learner 121-4 that will be described later.

The model learner 121-4 may train a cognitive impairment diagnosis model used for the cognitive impairment diagnosis and prediction, using learning data. The model learner 121-4 may generate a causal relationship between the features extracted from the electroencephalogram signal and cognitive impairment-related information and output a degree of a cognitive impairment and a cause of the cognitive impairment on the basis pieces of cognitive impairment diagnosis data related to cognitive impairments acquired from a plurality of users. Cognitive impairment diagnosis data of a user acquired by a brain-related expert may include information related to a degree of a cognitive impairment of the user and a cause of the cognitive impairment. In this case, the cognitive impairment diagnosis model may be a model that learns using an artificial neural network algorithm.

For example, the cognitive impairment diagnosis model may amplify the electroencephalogram signal, remove noise from a frequency domain included in the electroencephalogram signal, and analyze the electroencephalogram signal to extract features.

The model learner 121-4 may output cognitive impairment diagnosis and prediction information of the user, using position information in which abnormality in neuroactivity is observed using features related to a degree of atrophy of each part of cerebral cortex and/or features related to a degree of ischemic damage of cerebral white matter, a current concentration in each frequency band, absolute or relative power, ratios between frequency bands, statistical comparison values with normal persons of the same age, and the like that are extracted from the electroencephalogram signal.

The model learner 121-4 learns to output the cognitive impairment diagnosis and prediction information (the degree of the cognitive impairment, the cause of the cognitive impairment, and the like) of the user using the features extracted from the electroencephalogram signal.

The cognitive impairment diagnosis model may be constructed considering an application field of a recognition model, an aim of learning, a computer performance of a device, and the like. The cognitive impairment diagnosis model may be, for example, a neural network-based model. For example, a model, such as a deep neural network (DNN), a recurrent neural network (RNN), a bidirectional recurrent deep neural network (BRDNN), or the like, may be used as the cognitive impairment diagnosis model, but the cognitive impairment diagnosis model is not limited thereto.

Also, the model learner 121-4 may train the cognitive impairment diagnosis model, for example, through supervised learning using learning data as an input value. In addition, the model learner 121-4, for example, may self-learn a type of data needed for the cognitive impairment diagnosis and prediction without particular supervision to train the cognitive impairment diagnosis model through unsupervised learning that finds criteria for the cognitive impairment diagnosis and prediction. Moreover, the model learner 121-4, for example, may train the cognitive impairment diagnosis model through reinforcement learning that uses feedback on whether results of the cognitive impairment diagnosis and prediction according to learning are correct.

Furthermore, when the cognitive impairment diagnosis model is trained, the model learner 121-4 may store the trained cognitive impairment diagnosis model. In this case, the model learner 121-4 may store the trained cognitive impairment diagnosis model in a memory of an electronic device including the data recognizer 122. Alternatively, the model learner 121-4 may store the trained cognitive impairment diagnosis model in a memory of an electronic device including the data recognizer 122 that will be described later. Alternatively, the model learner 121-4 may store the trained cognitive impairment diagnosis model in a memory of a server that is connected to an electronic device through a wired or wireless network.

In this case, a memory in which the trained cognitive impairment diagnosis model is stored may also store, for example, instructions or data related to at least one other component of an electronic device. Also, the memory may store software and/or a program. The program may include, for example, kernel, middleware, an application programming interface (API), and/or an application program (or an "application").

The model evaluator 121-5 may input evaluation data into the cognitive impairment diagnosis model and, when recognition results output from the evaluation data do not satisfy preset criteria, enable the model learner 121-4 to relearn. In this case, the evaluation data may be preset data for evaluating the cognitive impairment diagnosis model.

For example, when the number or a ratio of pieces of the evaluation data, evaluating that the results of the cognitive impairment diagnosis and prediction are not accurate among recognition results of the trained cognitive impairment diagnosis model output from the evaluation data, exceeds a preset threshold value, the model evaluator 121-5 may evaluate that the recognition results do not satisfy the preset criteria.

When a plurality of trained cognitive impairment diagnosis models exist, the model evaluator 121-5 may evaluate that each of the trained cognitive impairment diagnosis models satisfies the preset criteria and determine the cognitive impairment diagnosis model satisfying the preset criteria as the final cognitive impairment diagnosis model. In this case, when a plurality of cognitive impairment diagnosis models satisfy the preset criteria, the model evaluator 121-5 may determine any one of cognitive impairment diagnosis models preset in order of high evaluation scores or the preset number of cognitive impairment diagnosis models as the final cognitive impairment diagnosis model.

At least one selected from the data acquirer 121-1, the preprocessor 121-2, the learning data selector 121-3, the model learner 121-4, and the model evaluator 121-5 in the data learner 121 may be manufactured in the form of at least one hardware chip and mounted on an electronic device. For example, at least one selected from the data acquirer 121-1, the preprocessor 121-2, the learning data selector 121-3, the model learner 121-4, and the model evaluator 121-5 may be manufactured in the form of a dedicated hardware chip for artificial intelligence or may be manufactured as part of an existing general purpose processor (e.g., a CPU or an application processor) or a graphics-only processor (e.g., a GPU) and mounted on various types of electronic devices as mentioned above.

Also, the data acquirer 121-1, the preprocessor 121-2, the learning data selector 121-3, the model learner 121-4, and the model evaluator 121-5 may be mounted on one electronic device or may be respectively mounted on separate electronic devices. In addition, at least one selected from the data acquirer 121-1, the preprocessor 121-2, the learning data selector 121-3, the model learner 121-4, and the model evaluator 121-5 may be embodied as a software module. When at least one selected from the data acquirer 121-1, the preprocessor 121-2, the learning data selector 121-3, the model learner 121-4, and the model evaluator 121-5 is embodied as a program module including a software module (or an instruction), the software module may be stored in non-transitory computer-readable recording media.

A structure of the data recognizer 122 will now be described.

The data recognizer 122 according to an embodiment may include a data acquirer 122-1, a preprocessor 122-2, a recognition data selector 122-3, a recognition result provider 122-4, and a model updater 122-5.

The data acquirer 122-1 may acquire data needed for the cognitive impairment diagnosis and prediction, and the preprocessor 122-2 may preprocess the acquired data to enable the acquired data to be used for the cognitive impairment diagnosis and prediction. The preprocessor 122-2 may process the acquired data in a preset format to enable the recognition result provider 122-4 to use the acquired data for the cognitive impairment diagnosis and prediction.

In detail, the preprocessor 122-2 may amplify the electroencephalogram signal.

The preprocessor 122-2 may amplify the electroencephalogram signal of the user, filter the frequency domain, and remove noise included in the electroencephalogram signal.

The preprocessor 122-2 may extract the features of the electroencephalogram signal after filtering and removing noise. The preprocessor 122-2 may extract features using the brain's connectivity and effective connectivity-based network model.

The preprocessor 122-2 may acquire, from the electroencephalogram signal, the features related to the degree of atrophy of each part of the cerebral cortex and/or the features related to the degree of ischemic damage of the cerebral white matter as data. The preprocessor 122-2 may extract, as data, a current concentration in each frequency, absolute power or relative power, ratios between frequency bands, statistical comparison values with the normal persons of the same age, and the like for the electrical signals in the brain. The preprocessor 122-2 may extract, from the electroencephalogram signal, position information in which abnormality in neuroactivity is observed, using the current concentration in each frequency, the absolute or relative power, the ratios between the frequency bands, the statistical comparison values with the normal persons of the same age, and the like.

The recognition data selector 122-3 may select data needed for the cognitive impairment diagnosis and prediction from the preprocessed data. The selected data may be provided for the recognition result provider 122-4. The recognition data selector 122-3 may select all or part of the preprocessed data according to the preset criteria for the cognitive impairment diagnosis and prediction. Also, the recognition data selector 122-3 may select the data according to the criteria preset by learning by the model learner 122-4.

The recognition result provider 122-4 may apply the selected data to the cognitive impairment diagnosis model to determine the cognitive impairment diagnosis and prediction information (the degree of the cognitive impairment, the cause of the cognitive impairment, and the like). The recognition result provider 122-4 may output the cognitive impairment diagnosis and prediction information of the user using position information in which abnormality in neuroactivity is observed using the features related to the degree of atrophy of each part of the cerebral cortex and/or the features related to the degree of ischemic damage of the cerebral white matter, absolute power and relative power of a power spectrum of the electroencephalogram, the magnitude of each frequency component of the power spectrum of the electroencephalogram, an alpha peak frequency of the electroencephalogram, ratios and coupling between different frequency bands of the electroencephalogram, connectivity of each position of a ring electroencephalogram, complexity of the electroencephalogram, and a current concentration in each frequency band in a cortical area, absolute or relative power, ratios and coupling between frequency bands, connectivity and synchronicity of each area, complexity, statistical comparison values thereof with the normal persons of the same age, and the like that are calculated from the electroencephalogram signal.

The recognition result provider 122-4 may provide a recognition result, related to the cognitive impairment diagnosis and prediction, that is a recognition aim of data. The recognition result provider 122-4 may use the data selected by the recognition data selector 122-3 as an input value to apply the selected data to the cognitive impairment diagnosis model. Also, the recognition result may be determined by the cognitive impairment diagnosis model and may include information and the like related to a degree of the cognitive impairment and a cause of the cognitive impairment according to a progression degree of the cognitive impairment, age, gender, and the like of the user.

The model updater 122-5 may update the cognitive impairment diagnosis model on the basis of an evaluation of the recognition result provided by the recognition result provider 122-4. For example, the model updater 122-5 may provide the model learner 122-4 with the recognition result provided by the recognition result provider 122-4 to enable the model learner 122-4 to update the cognition impairment diagnosis model.

At least one selected from the data acquirer 122-1, the preprocessor 122-2, the recognition data selector 122-3, the recognition result provider 122-4, and the model updater 122-5 in the data recognizer 122 may be manufactured in the form of at least one hardware chip and mounted on an electronic device. For example, at least one selected from the data acquirer 122-1, the preprocessor 122-2, the recognition data selector 122-3, the recognition result provider 122-4, and the model updater 122-5 may be manufactured in the form of a dedicated hardware chip for artificial intelligence (AI) or may be manufactured as part of an existing general purpose processor (e.g., a CPU or an application processor) or a graphics-only processor (e.g., a GPU) and mounted on various types of electronic devices as mentioned above.

Figure 15:
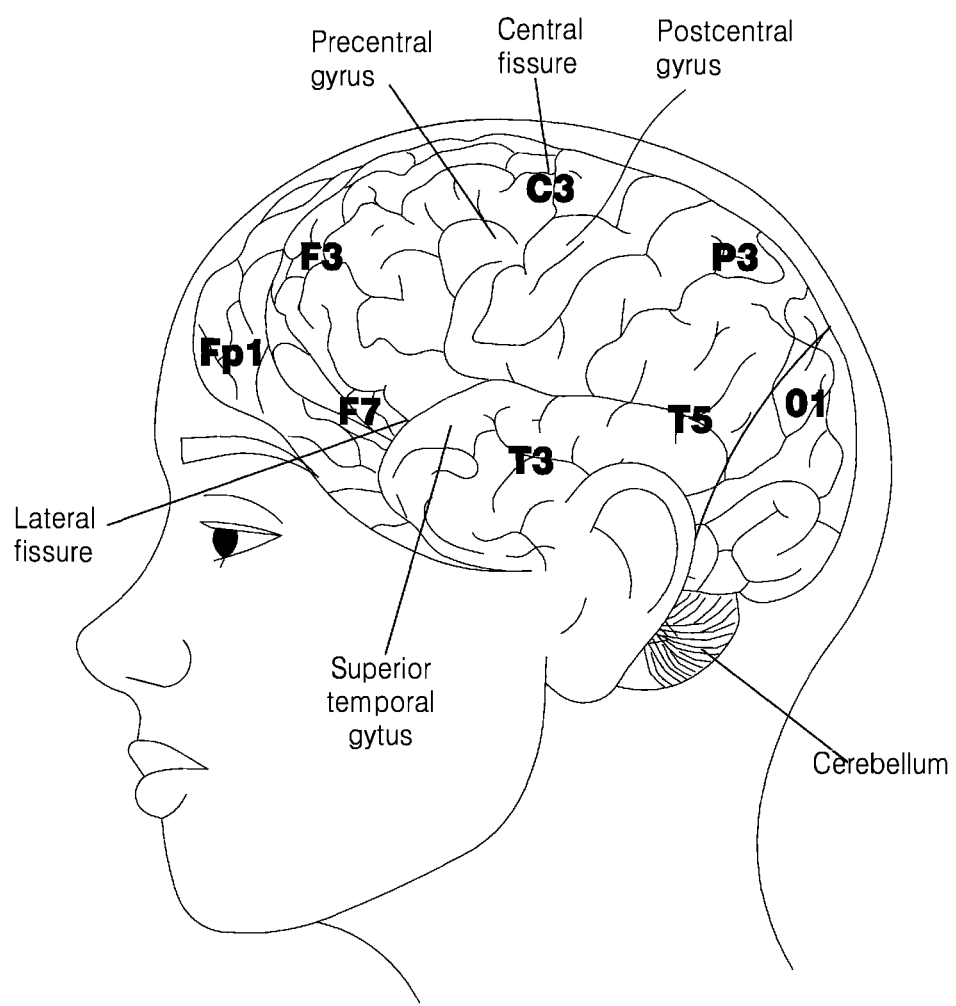
FIG. 15 illustrates a plurality of positions constituting a brain and channels respectively allocated to the plurality of positions constituting the brain, according to an embodiment.

FIG. 15 illustrates a plurality of positions constituting a brain and channels respectively allocated to the plurality of positions constituting the brain, according to an embodiment.

All of channels respectively allocated to parts of a brain conform to international 10-5/10/20 system. In the present disclosure, 19 channels are used as the number of most commonly used electrodes, but the number of electrodes is not limited to 19 channels and thus may be less or more than these. The channels are classified into; Fp1 and Fp2 that are positioned in a prefrontal part of a brain lobe that is positioned in front of cerebral hemispheres and has functions of memory, thinking, and the like; F7, F3, Fz, F4, and F8 that are positioned in a frontal lobe part of the brain lobe; C3, Cz, and C4 that are positioned in a central part of the brain lobe; T3, T4, T5, and T6 that are positioned in a temporal lobe part that is a cortical area in which hippocampus taking charge of hearing information and memory is positioned; P3, Pz, and P4 that are positioned in a parietal lobe part that spans outer and inner surfaces of brain cortex, includes sensory neurons, and is involved in primary somatosensory functions, sensory integration, spatial recognition, and the like; and O1 and O2 that are positioned in an occipital lobe part that is positioned in the back of the brain and is adjacent to a visual field to analyze and integrate visual information.

Figure 16:
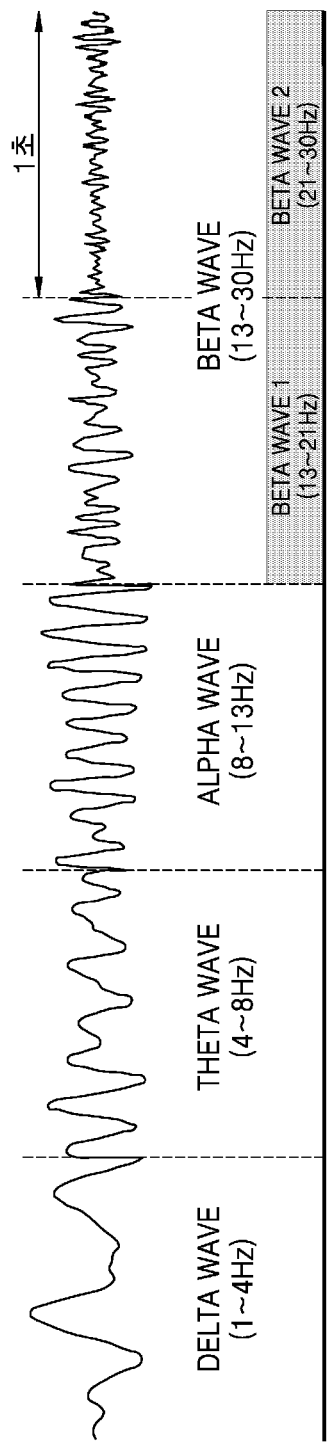
FIG. 16 illustrates an example of a frequency band of an electroencephalogram and a range of a waveform.

FIG. 16 illustrates an example of a frequency band of an electroencephalogram and a range of a waveform.

An electroencephalogram of a human body is classified into a delta ($\delta$) wave, a theta ($\theta$) wave, an alpha ($\alpha$) wave, a beta ($\beta$) wave, a gamma ($\gamma$) wave, and the like according to a frequency range thereof. Contents according to an embodiment include a delta ($\delta$) wave, a theta ($\theta$) wave, alpha ($\alpha$) wave 1, alpha ($\alpha$2) wave 2, beta ($\beta$) wave 1, beta ($\beta$) wave 2, beta ($\beta$) wave 3, and a gamma ($\gamma$) wave.

The delta ($\delta$) wave shows a frequency of about 1 Hz to about 4 Hz and an amplitude of about 20 $\mu$V to about 200 $\mu$V and appears in a deep sleep state of a normal person or in a newborn baby. The theta ($\theta$) wave shows a frequency of about 4 Hz to about 8 Hz and an amplitude of about 20 $\mu$V to about 100 $\mu$V and appears in an emotionally stable state or a sleeping state. The alpha ($\alpha$) wave shows a frequency of about 8 Hz to about 12 Hz and an amplitude of about 20 $\mu$V to about 60 $\mu$V and appears in a comfortable state in which tension is relaxed, and the amplitude increases in a stable state. Contents according to an embodiment classify an alpha wave into alpha ($\alpha$) wave 1 of about 8 Hz to about 10 Hz and alpha ($\alpha$) wave 2 of about 10 Hz to about 12 Hz or about 13 HZ. A beta ($\beta$) wave shows a frequency of 12 Hz or 13 Hz or more and an amplitude about 2 $\mu$V to about 20 $\mu$V and appears in an awake or conscious state. Contents according to an embodiment classify a beta wave into beta ($\beta$) wave 1, beta ($\beta$) wave 2, and beta ($\beta$) wave 3 according to aims. A gamma ($\gamma$) wave has a frequency band of 30 Hz or more but may be variously set according to aims.

The device described above may be embodied as hardware components, software components, and/or a combination of hardware components and software components. For example, the device and components described in the embodiments may be embodied by using one or more general purpose computers or special purpose computers such as a processor, a controller, an arithmetic logic unit (ALU), a digital signal processor, a microcomputer, a field programmable gate array (FPGA), a programmable logic unit (PLU), a microprocessor, or any other devices capable of executing and responding to instructions. A processing unit may execute an operating system (OS) and one or more software applications executed on the OS. In addition, the processing unit may access, store, manipulate, process, and generate data in response to the execution of software. For convenience of description, one processing unit may be described as being used, but one of ordinary skill in the art may understand that the processing unit may include a plurality of processing elements and/or a plurality of types of processing elements. For example, the processing unit may include a plurality of processors or one processor and one controller. Also, the processing unit may include another processing configuration such as a parallel processor.

Software may include computer program, code, instructions, or a combination of one or more thereof, and configure the processing unit to operate as wanted or independently or collectively instruct the processing unit. Software and/or data may be permanently or temporarily embodied in any type of machine, a component, a physical device, virtual equipment, a computer storage medium or device, or transmitted signal waves to be interpreted by the processing unit or to provide the processing unit with instructions or data. The software may be distributed over networked computer systems to be stored or executed in a distributed manner. The software and data may be stored in one or more computer-readable recording media.

The method according to the embodiments may be embodied in the form of program instructions that may be executed through various types of computer means and then recorded in a computer-readable recording medium. The computer-readable recording medium may include program instructions, data files, data structures, and the like alone or in combination. The program instructions recorded on the computer-readable recording medium may be particularly designed and configured for the embodiments or may be well known to and used by one of ordinary skill in computer software art. Examples of the computer-readable recording medium include magnetic media such as a hard disk, a floppy disk, and a magnetic tape, optical media such as CD-ROM and DVD, magneto-optical media such as a floptical disk, and a hardware device particularly configured to store and execute program instructions such as ROM, RAM, flash memory, and the like. Examples of the program instructions include not only machine language code generated by a compiler, but also high-level language code that may be executed by a computer by using an interpreter or the like. The hardware device described above may be configured to operate as one or more software modules so as to perform operations of the embodiments, and the reverse thereof is the same.

Although the embodiments have been described above by limited embodiments and drawings, various modifications and changes may be made from the above description by one of ordinary skill in the art. For example, the described techniques may be performed in a different order than the described method, and/or components of the described system, structure, device, circuit, and the like may be combined or joined in a different form than the described method, or even if replaced or substituted by other components or equivalents, and an appropriate result may be achieved.

Therefore, other embodiments, other aspects, and equivalents to claims also belong to the scope of claims that will be described below.

Embodiments of the present disclosure relate to a cognitive impairment diagnosis method and a computer program.

The invention claimed is:

1. A cognitive impairment diagnosis method comprising:
   receiving an electroencephalogram signal of a user by a cognitive impairment diagnosis device;
   preprocessing the electroencephalogram signal by the cognitive impairment diagnosis device;
   extracting features, by the cognitive impairment diagnosis device, from the preprocessed electroencephalogram signal by using a brain connectivity-based analysis method;
   inferring, by the cognitive impairment diagnosis device, a degree of atrophy of each part of cerebral cortex and a degree of ischemic damage of cerebral white matter of a user, using at least one selected from a current concentration in each frequency band, an absolute power in each frequency band, a relative power in each frequency band, ratios between the frequency bands, and a statistical comparative data with values of a normal person of the same age;
   determining, by the cognitive impairment diagnosis device, a cause of the cognitive impairment as a neurodegenerative cognitive impairment disease when the degree of atrophy of each part of the cerebral cortex is greater than the degree of ischemic damage of the cerebral white matter; and
   determining, by the cognitive impairment diagnosis device, the cause of the cognitive impairment as vascular dementia when the degree of atrophy of each part of the cerebral cortex is less than the degree of ischemic damage of the cerebral white matter.

2. A computer program stored on a non-transitory computer-readable recording medium to execute the method of claim 1 using a computer.

* * * * *